(12) United States Patent
Iizuka

(10) Patent No.: US 12,245,814 B2
(45) Date of Patent: Mar. 11, 2025

(54) REFRACTION MEASURING APPARATUS

(71) Applicant: HOYA LENS THAILAND LTD., Pathumthani (TH)

(72) Inventor: Takashi Iizuka, Tokyo (JP)

(73) Assignee: HOYA LENS THAILAND LTD., Pathumthani (TH)

( * ) Notice: Subject to any disclaimer, the term of this patent is extended or adjusted under 35 U.S.C. 154(b) by 800 days.

(21) Appl. No.: 17/485,873

(22) Filed: Sep. 27, 2021

(65) Prior Publication Data

US 2022/0095915 A1  Mar. 31, 2022

(30) Foreign Application Priority Data

Sep. 28, 2020 (JP) ................................ 2020-161774

(51) Int. Cl.
*A61B 3/00* (2006.01)
*A61B 3/15* (2006.01)
*G01N 21/41* (2006.01)

(52) U.S. Cl.
CPC ............ *A61B 3/152* (2013.01); *A61B 3/0008* (2013.01); *G01N 21/4133* (2013.01)

(58) Field of Classification Search
CPC ... A61B 3/152; A61B 3/0008; G01N 21/4133
See application file for complete search history.

(56) References Cited

U.S. PATENT DOCUMENTS

| 2,933,977 A | 4/1960 | Landis |
| 3,841,760 A | 10/1974 | Guyton |

(Continued)

FOREIGN PATENT DOCUMENTS

| CN | 106249412 A | 12/2016 |
| CN | 111616674 A | 9/2020 |

(Continued)

OTHER PUBLICATIONS

Dec. 13, 2023 Office Action issued in European Patent Application No. 19902783.0.

(Continued)

*Primary Examiner* — Wen Huang
(74) *Attorney, Agent, or Firm* — Oliff PLC

(57) ABSTRACT

A refraction measuring apparatus measures refractive properties of an eye by two light bundles respectively passing through two apertures, the apparatus including: a first rotational member, rotatably supported about a first rotational center, provided with the two apertures on either side of the first rotational center; a second rotational member, rotatably supported about a second rotational center, provided with a light-transmission portion(s) and a light-shielding portion at different rotational-direction positions. When the first rotational member is rotated, the second rotational member rotates, and while an aperture arrangement direction of the two apertures changes in accordance with the rotation of the second rotational member, a light-transmission state is entered, in which the light-transmission portion coincides with the two apertures to allow the two light bundles to pass through, or a light-shielding state is entered, in which the light-shielding portion coincides with the two apertures to shield the two light bundles.

11 Claims, 15 Drawing Sheets

(56) References Cited

U.S. PATENT DOCUMENTS

| | | | |
|---|---|---|---|
| 4,134,644 | A | 1/1979 | Marks et al. |
| 4,778,268 | A | 10/1988 | Randle |
| 4,943,151 | A | 7/1990 | Cushman |
| 4,973,151 | A | 11/1990 | Bryant |
| 5,988,814 | A | 11/1999 | Rohlfing et al. |
| 6,687,003 | B1 | 2/2004 | Sorensen et al. |
| 7,370,964 | B2 | 5/2008 | Wakil et al. |
| 8,783,871 | B2 | 7/2014 | Pamplona et al. |
| 9,271,646 | B2 | 3/2016 | Neal et al. |
| 10,278,573 | B2 | 5/2019 | Boutinon et al. |
| 10,980,412 | B2 | 4/2021 | Takii et al. |
| 2002/0140903 | A1 | 10/2002 | Schachar |
| 2004/0032567 | A1 | 2/2004 | Fukuma et al. |
| 2004/0032568 | A1 | 2/2004 | Fukuma et al. |
| 2016/0363770 | A1 | 12/2016 | Kim et al. |
| 2018/0242837 | A1 | 8/2018 | Nauche et al. |
| 2020/0221943 | A1 | 7/2020 | Kobayashi et al. |
| 2021/0386285 | A1* | 12/2021 | Walsh .................. A61B 3/0025 |

FOREIGN PATENT DOCUMENTS

| | | |
|---|---|---|
| EP | 1138253 A2 | 10/2001 |
| EP | 1433415 A2 | 6/2004 |
| EP | 1 752 084 A2 | 2/2007 |
| EP | 3106911 A1 | 12/2016 |
| EP | 3903663 A1 | 11/2021 |
| GB | 148754 A | 1/1921 |
| JP | 2001-340296 A | 12/2001 |
| JP | 6308277 B2 | 4/2018 |
| JP | 2020-103743 A | 7/2020 |
| KR | 10-2016-0147636 A | 12/2016 |
| WO | 2002/078530 A1 | 10/2002 |
| WO | 2015/118634 A1 | 8/2015 |
| WO | 2016/204433 A1 | 12/2016 |
| WO | 2017/037386 A1 | 3/2017 |

OTHER PUBLICATIONS

U.S. Appl. No. 17/312,835, filed Jun. 10, 2021 in the name of inventor Takashi Iizuka.

May 1, 2024 Office Action issued in U.S. Appl. No. 17/312,835.

Victor F. Pamplona et al: "NETRA: Interactive Display for Estimating Refractive Errors and Focal Range," ACM Transactions on Graphics, ACM, NY, US, vol. 29, No. 4, Jul. 26, 2010, 77:1-77:8.

Jan. 27, 2022 Extended European Search Report issued in European Patent Application No. 19902783.0.

Sep. 6, 2022 Office Action issued in Japanese Patent Application No. 2018-247322.

Nov. 1, 2023 Office Action issued in Chinese Patent Application No. 201980086436.8.

Mar. 3, 2020 International Search Report issued in International Patent Application No. PCT/JP2019/048380.

Thibos N. Larry, "Principles of Hartmann-Shack Aberrometry", Journal of Refractive Surgery, Oct. 31, 2000, vol. 16, pp. S563-S565.

Feb. 8, 2022 Extended European Search Report issued in European Patent Application No. 21199310.0.

Oct. 29, 2024 Office Action issued in U.S. Appl. No. 17/312,835.

* cited by examiner

REFRACTION MEASURING APPARATUS

BACKGROUND OF THE INVENTION

1. Field of the Invention

The present disclosure relates to a refraction measuring apparatus for measuring refractive properties of the human eye.

2. Description of Related Art

When prescribing eyeglasses or contact lenses, a refraction test is performed to measure the refractive properties of the eye. Subjective testing in which the examinee identifies the visibility of the presented visual target (marker) or light, and objective testing in which light rays that are incident on the eyeball are externally observed, are examples of refraction tests that are known in the art.

As an example of subjective testing, an examination utilizing interchangeable lenses (lens elements) is widely used to find an optimal dioptric power (the refractive power toward the positive side that obtains the best visual acuity) by (the optometrist) changing the corrective lens placed in front of the examinee's eye while the examinee views a vision chart (e.g., an optotype). Such a type of examination utilizing interchangeable lenses has the advantage of being able to be performed using a simple structure that includes a holder member and a corrective lens group (optometric lens set) that is mounted on the holder member. On the other hand, since it is necessary to repetitively carry out the same visual acuity test while exchanging a large number of corrective lenses, this operation tends to be cumbersome and is a large burden on the examinee and the person conducting the measurement (e.g., an optometrist). Furthermore, there is also the difficult task of achieving a correct judgement, since such a type of examination is reliant on the examinee memorizing how he/she saw with the previously worn corrective lens and comparing how he/she sees with the subsequently worn corrective lens.

In a phoropter, which is an examination apparatus having a plurality of pre-set corrective lenses, the troublesome task of exchanging the corrective lenses is reduced. However, compared to a holder member having a small and simple structure, a phoropter requires a lot of space for installment and the apparatus itself tends to be expensive.

Although an examination apparatus such as an autorefractometer, etc., that is used in objective testing can achieve an efficient examination in a short period of time without requiring skill from the person conducting the measurement, such an examination apparatus is extremely costly. Moreover, a large space for installment is required.

In view of the above-described problems, Patent Literature 1 (Japanese Unexamined Patent Publication No. 2020-103743) proposes an apparatus and method in which an eye refraction test can be performed by subjective testing. Such an apparatus and method utilize the Scheiner principle, in which a measurement disc, which is provided in front of the eye, is provided with two (pinhole) apertures, through which light is restricted (narrowed down) and passed through the two apertures, and the eye's refraction properties are measured based on how the eye views a first light bundle and a second light bundle (the positional relationship of the images) that pass through the two apertures and reach the retina. In the disclosure of Patent Literature 1, different transmissive properties are established at the two apertures so that by setting the first light bundle and the second bundle to respectively transmit through only one of the apertures, a high-precision examination is achieved.

There is a demand to reduce the workload as much as possible and to achieve efficient examination when carrying out a refraction test that applies an apparatus and a method such as is described in Patent Literature 1. Specifically, when refractive tests are performed on both eyes, it is desired to be able to quickly switch the eye to be examined without having to change the measuring disc, provided with the (two) apertures, for each eye. Furthermore, when examining one eye, it is necessary to prevent excess light from entering the other eye, and it is desirable to make the structure and operation for shielding the eye on the side that is not to be examined as simple as possible. In order to obtain an accurate prescription value, it is necessary to examine the refractive properties of the eye in a plurality of directions, and it is desirable to be able to easily and reliably change the orientation of the apertures (aperture arrangement direction) in the measurement disc to a plurality of directions.

SUMMARY OF INVENTION

In view of the aforementioned problems, the illustrated embodiments of the invention provide a refraction measuring apparatus that can perform a high-precision eye refraction test easily and at low cost.

In an embodiment, a refraction measuring apparatus, is provided, that measures refractive properties of an eye based on respective images formed by first and second light bundles, emanating from a light emitter, the first and second light bundles respectively passing through first and second apertures, provided at a same distance away from the light emitter, and concurrently incident on the eye, the refraction measuring apparatus comprising, at respective positions corresponding to a pair of the eyes: a first rotational member, rotatably supported on a support member about a first rotational center, provided with the first aperture and the second aperture on either side of the first rotational center; a second rotational member, rotatably supported about a second rotational center, at a different position from the first rotational center, the second rotational member provided with at least one light-transmission portion and a light-shielding portion at different positions in a rotational direction about the second rotational center. When the first rotational member is rotated relative to the support member, the second rotational member rotates in association with the rotation of the first rotational member, and, while an aperture arrangement direction of the first and second apertures changes in accordance with the rotation of the second rotational member, the refraction measuring apparatus enters one of: a light-transmission state in which the light-transmission portion coincides with the first and second apertures to allow the first and second light bundles to pass through the first and second apertures, and a light-shielding state in which the light-shielding portion coincides with the first and second apertures to shield the first and second light bundles.

It is desirable for the refraction measuring apparatus to be further provided with a gear mechanism for rotating the second rotational member about the second rotational center at a different angle of rotation to a unit angle-of-rotation of the first rotational member about the first rotational center.

As an example of a gear mechanism, annular internal teeth, centered about the first rotational center, may be fixedly provided on the support member. The second rotational member is rotatably supported on the first rotational member about the second rotational center, the second rotational member is provided with outer teeth which mesh with the internal teeth, and, when the first rotational member rotates, the second rotational member rotates while changing a meshing position between the internal teeth and the outer teeth.

As another example of a gear mechanism, the second rotational member may be rotatably supported on the support member about the second rotational center, and the first rotational member and the second rotational member may be respectively provided with outer teeth, each having a mutually different number of teeth. A drive gear is further provided which meshes with the outer teeth of the first rotational member and the outer teeth of the second rotational member, and, when the drive gear rotates, the first rotational member and the second rotational member rotate while changing a meshing position between the drive gear and the respective outer teeth of the first rotational member and the second rotational member.

As an example of a light-transmission portion, the light-transmission portion may include a plurality of openings formed through the second rotational member at different positions in a rotational direction about the second rotational center. In the light-transmission state, the first and second apertures coincide with each respective opening of the plurality of openings, oriented in a plurality of aperture arrangement directions about the first rotational center, to thereby allow the first and second light bundles to pass through the first and second apertures.

It is desirable for four of the openings to be provided in the second rotational member, wherein the first and second apertures coincide with each respective opening of the four openings per a 45-degree rotation of the first rotational member.

As an example of a light-transmission portion, the light-transmission portion may include a continuous opening formed continuously in a rotational direction about the second rotational center. In the light-transmission state, the first and second apertures allow the first and second light bundles to pass therethrough while continuously changing the aperture arrangement direction within a range defined by the continuous opening.

In another embodiment, a refraction measuring apparatus, is provided, that measures refractive properties of an eye based on respective images formed by first and second light bundles, emanating from a light emitter, the first and second light bundles respectively passing through first and second apertures, provided at a same distance away from the light emitter, and concurrently incident on the eye, the refraction measuring apparatus including: rotational members, rotatably supported at positions that correspond to a pair of the eyes, respectively. Each rotational member is provided with a plurality of groups of the first and second apertures, and a light-shielding portion, at respective positions that are positioned eccentrically from the rotational center of an associated rotational member. While respective aperture arrangement directions of the plurality of groups of the first and second apertures change in accordance with a change in an angular position of the associated rotational member in the rotational direction, the refraction measuring apparatus enters one of: a light-transmission state in which the first and second light bundles pass through, at either side of an axis of vision, one group of the first and second apertures at a time, and a light-shielding state in which the light-shielding portion shields the first and second light bundles from a field-of-view area.

Hence, a light-transmission state, in which the refraction properties of the eye are measured at a plurality of orientations, and a light-shielding state, in which the first light bundle and the second light bundle that are used for measurement are shielded, occur according to the rotation of the rotational member. Accordingly, a refraction measuring apparatus can be easily achieved at low cost, and a high-precision eye refraction test can be performed with superior workability and with less time and effort.

The present disclosure relates to subject matter contained in Japanese Patent Application No. 2020-161774 (filed on Sep. 28, 2020) which is expressly incorporated herein in its entirety.

BRIEF DESCRIPTION OF THE DRAWINGS

Embodiments and examples of the invention will be discussed below in detail with reference to the accompanying drawings, in which.

DESCRIPTION OF THE EMBODIMENTS

Figure 1:
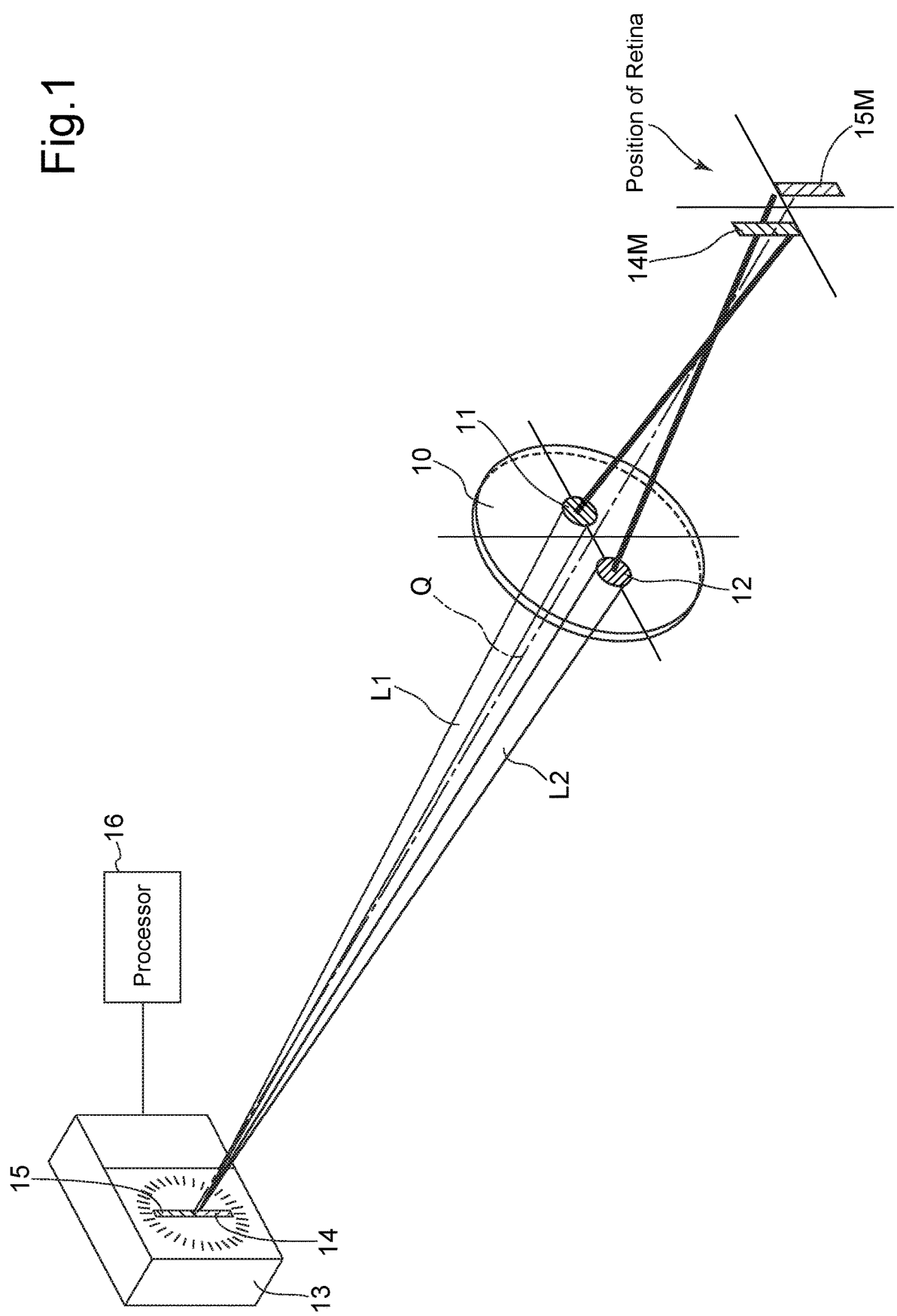
FIG. 1 shows an explanatory diagram of measuring refraction properties of the eye using a refraction measuring apparatus according to an embodiment of the present invention.

Firstly, an overview of an eye refraction test (measurement of the refractive properties) using a refraction measuring apparatus of the present disclosure will be described with reference to FIGS. 1 through 4. This measurement of the refractive properties of the eye utilizes the Scheiner principle in which light bundles passing through two separate apertures refract at a lens element, intersect (meet) at a focal position to become one light bundle, and thereafter, separate into two light bundles again at a position away from the focal position.

A flat plate-shaped measurement disc 10 is provided with a first aperture 11 and a second aperture 12. The first aperture 11 and the second aperture 12 are pinhole-shaped round apertures that are formed through the measurement disc 10. The size (diameter) of the first aperture 11 and the second aperture 12 is the same. Furthermore, the size and mutual distance between the central axes of the first aperture 11 and the second aperture 12 are determined in order for the Scheiner principle to manifest. The direction in which the first aperture 11 and the second aperture 12 are arranged (the direction of a line connecting the respective centers of the first aperture 11 and the second aperture 12) is defined as the aperture arrangement direction. It should be noted that the first aperture 11 and the second aperture 12 may be slit-shaped apertures; in such a case, the two slits are arranged in parallel to each other.

A light-emission device (light emitter) 13, is provided, which emits a first light bundle L1 and a second light bundle L2 toward the measurement disc 10, at the same distance from the light-emission device 13. The light-emission device 13 is provided with two rectangular-shaped visual markers 14 and 15 on a light-emission surface of the light-emission device 13; the first light bundle L1 is distributed (emanated) from the visual marker 14 and the second light bundle L2 is distributed (emanated) from the visual marker 15. In the light-emission device 13, it is possible to change the relative positions of the visual marker 14 and the visual marker 15 along the aperture arrangement direction of the measurement disc 10. Furthermore, it is possible to change the angular positions of the visual marker 14 and the visual marker 15 about an axis that is normal to the light-emission surface (an axis passing through the boundary between the visual marker 14 and the visual marker 15) of the light-emission device 13. Radial indicators, which are a guide for the angular position (of the visual markers 14 and 15) are formed around the visual marker 14 and the visual marker 15.

The light distribution from the light-emission device 13 can selected from various configurations. For example, the visual marker 14 and the visual marker 15 can be formed as a mask that separates light that is emitted from a light source by partially allowing the light to pass through the mask. Alternatively, a surface light source (display) may be used to emit light regions that form the visual marker 14 and the visual marker 15. Alternatively, the visual marker 14 and the visual marker 15 can be provided as light-reflection portions, whereby reflection light reflected by the visual markers 14 and 15 is distributed as the first light bundle L1 and the second light bundle L2.

An optical element such as an optical filter, etc., is used so that the first light bundle L1 does not pass through the second aperture 12 and the second light bundle L2 does not pass through the first aperture 11, so that the light-emission device 13 can have selective transmissive properties. For example, mutually different wavelength bands of the first light bundle L1 and the second light bundle L2 may be set, and thereafter, a color filter, having wavelength band that allows the first light bundle L1 to transmit therethrough and stops the second light bundle L2 from transmitting there-through, is provided on the first aperture 11 and a color filter, having wavelength band that allows the second light bundle L2 to transmit therethrough and stops the first light bundle L1 from transmitting therethrough, is provided on the second aperture 12. Alternatively, with the first light bundle L1 and the second light bundle L2 being linearly polarized with mutually different polarization characteristics, a polarization filter that is arranged in a direction to allow the first light bundle L1 to transmit therethrough and to stop the second light bundle L2 from transmitting therethrough may be provided on the first aperture 11, and another polarization filter that is arranged in a direction to allow the second light bundle L2 to transmit therethrough and to stop the first light bundle L1 from transmitting therethrough may be provided on the second aperture 12.

The measurement disc 10 is arranged (positioned) between the light-emission device 13 and the examinee's eye so that an axis of vision Q of the examinee's eye passes along an intermediate axis between the first aperture 11 and the second aperture 12. The measurement disc 10 narrows down (restricts) the first light bundle L1 and the second light bundle L2 (emitted from the light-emission device 13) via the first aperture 11 and the second aperture 12, respectively, while allowing the first light bundle L1 and the second light bundle L2 to pass therethrough and arrive at the retina of the eye. According to the above-described selective transmissive properties of the first aperture 11 and the second aperture 12, the first light bundle L1 only passes through the first aperture 11 to arrive at the retina of the eye, and the second light bundle 12 only passes through the second aperture 12 to arrive at the retina of the eye. Hence, the examinee views an image of the first light bundle L1 as a visual marker image 14M, corresponding to the visual marker 14, and views an image of the second light bundle L2 as a visual marker image 15M, corresponding to the visual marker 15.

Figure 2:
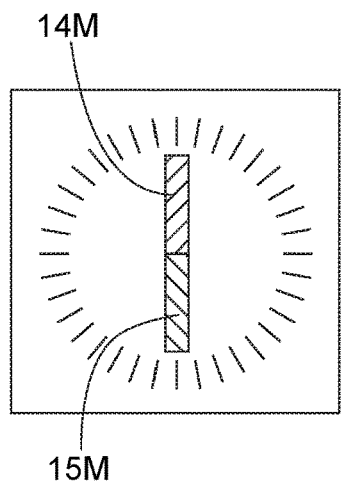
FIG. 2 is a schematic view of visual marker images that are formed by the refraction measuring apparatus of FIG. 1.

If the refraction properties of the eye are normal, i.e., appropriate and correct, the position at which the first light bundle L1 that passes through the first aperture 11 arrives and the position at which the second light bundle L2 that passes through the second aperture 12 arrives meet (align) with respect to the arrangement direction of the first aperture 11 and the second aperture 12. In such a case, the image formed by the first light bundle L1 and the image formed by the second light bundle L2 appear to the examinee as being aligned (positioned on top of each other) with respect to the arrangement direction of the first and second apertures 11 and 12. In other words, in the case where the rectangular visual markers 14 and 15 are in a linear arrangement on the light-emission device 13, the corresponding rectangular visual marker images 14M and 15M appear aligned in a linear arrangement, as shown in FIG. 2.

Figure 3:
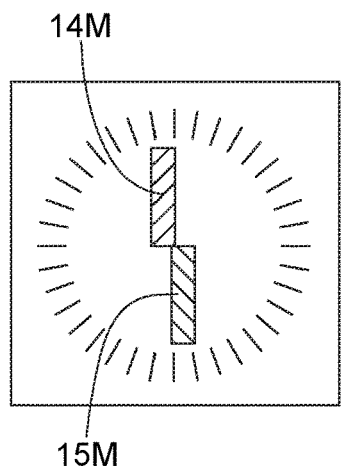
FIG. 3 is a schematic view of visual marker images that are formed by the refraction measuring apparatus of FIG. 1.
Figure 4:
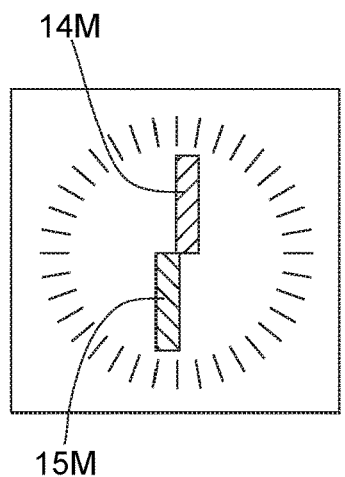
FIG. 4 is a schematic view of visual marker images that are formed by the refraction measuring apparatus of FIG. 1.

Whereas, if the refractive power of the eye is greater than the refractive power of a normal eye, the first light bundle L1 and the second light bundle L2 intersect before arriving at the retina. Conversely, if the refractive power of the eye is less than the refractive power of a normal eye, the first light bundle L1 and the second light bundle L2 arrive at the retina without intersecting at the retina nor without intersecting before arriving at the retina (the intersecting position of the first light bundle L1 and the second light bundle L2 is behind the retina); accordingly, in either of such cases, the image formed by the first light bundle L1 and the second light bundle L2 would appear to the examinee as shifted in the arrangement direction of the first and second apertures 11 and 12. In other words, in the case where the rectangular visual markers 14 and 15 are in a linear arrangement on the light-emission device 13, the corresponding rectangular visual marker images 14M and 15M appear out of alignment relative to a linear arrangement. FIG. 3 shows how the visual marker images 14M and 15M appear when the refractive power of the eye is greater than the refractive power of a normal eye, and FIG. 4 shows how the visual marker images 14M and 15M appear when the refractive power of the eye is less than the refractive power of a normal eye.

Hence, information on the refractive properties of the eye can be obtained based on how the image formed by the first light bundle L1 (visual marker image 14M) and the image formed by the second light bundle L2 (visual marker image 15M) appear. However, it is difficult to derive the refractive properties by quantitatively identifying, at the examinee's side, the deviation between the two images. Accordingly, the positional relationship of the visual marker 14 and the visual marker 15 are changed (adjusted), at the light-emission device 13, along the arrangement direction between the first and second apertures 11 and 12, to thereby establish an aligned state (linear arrangement) in which the image formed by the first light bundle L1 and the image formed by the second light bundle L2 appear aligned (the visual marker image 14M and the visual marker image 15M appear in a linear arrangement, positioned on top of each other), with respect to the arrangement direction of the first and second apertures 11 and 12, whereby the refractive power of the eye can be calculated from the positional relationship (the shift amount and shift direction) of the visual marker 14 and the visual marker 15 in such an aligned state.

The technique for changing the positions of the visual marker 14 and the visual marker 15 along the aperture arrangement direction differs depending on the configuration/structure of the light-emission device 13. For example, if the visual marker 14 and the visual marker 15 are formed as masks or light-reflection portions, these parts can be mechanically moved using a driver. If the visual marker 14 and the visual marker 15 are provided in the form of part of a display emitting light, then the light-emitting area of the display is changed.

A processor 16, which constitutes part of a refraction measuring apparatus, is provided in the form of a computer, etc., and controls the positional changes of the visual marker 14 and the visual marker 15 in the aperture arrangement directions. For example, the positions of the visual marker 14 and the visual marker 15 can be changed in accordance with an input operation by the examinee or the person conducting the measurement (e.g., an optometrist) with an input device such as, e.g., a keyboard or touch panel. Furthermore, the processor 16 obtains distance information, between the measurement disc 10 and the light-emission surface (on the light-emission device 13) of the first light bundle L1 and the second light bundle L2, from a distance sensor. Furthermore, the processor 16 calculates the refractive power of the eye based on positional-shift amounts of the visual marker 14 and the visual marker 15 along the aperture arrangement direction when the first light bundle L1 and the second light bundle L2 (the visual marker image 14M and the visual marker image 15M) are at the above-described aligned state on the retina. Regarding the calculation of the refractive power of the eye, the formula disclosed in the above-mentioned Patent Literature 1 (Japanese Unexamined Patent Publication No. 2020-103743) can be utilized.

By using the above-described refraction measuring apparatus, the refractive power of the eye can be measured very accurately by only having the examinee identify an aligned state of the visual marker image 14M and the visual marker image 15M. Since there is no need for the light-emission device 13 to perform a complex light-emission control, nor for the examinee or the person conducting the measurement (optometrist, etc.) to record shift amounts of the visual marker image 14M and the visual marker image 15M, the construction and control of the refraction measuring apparatus can be simplified, and the workload of the measuring operation can be reduced.

Furthermore, since the first light bundle L1 does not pass through the second aperture 12 and the second light bundle L2 does not pass through the first aperture 11, only two images simultaneously form on the retina: the visual marker image 14M and the visual marker image 15M. Hence, it is easy for the examinee to accurately determine (judge) whether or not any positional shift exists between the visual marker image 14M and the visual marker image 15M.

In the case where such selective transmissive properties of light are provided for the first aperture 11 and the second aperture 12, by using the above-mentioned color filters, the examinee can even more easily identify the positional relationship between the visual marker image 14M and the visual marker image 15M due to the difference in color of the first light bundle L1 and the second light bundle L2.

Since the refraction properties of the eye are dependent on the direction of orientation, in practice, it is necessary to perform the above-described measurement of refractive properties in a plurality of directions in an actual refraction test. Specifically, it is desirable to set the aperture arrangement direction of the first aperture 11 and the second aperture 12 in three or more directions out of a horizontal direction, a vertical direction, and intermediate directions in between the horizontal direction and the vertical direction, and to perform measurements in each direction.

In order to achieve measurements in such a plurality of directions, it is conceivable to provide a plurality of measurement discs 10 with the first aperture 11 and the second aperture 12 having different aperture arrangement directions, and, when performing the measurements in each direction, exchange and set each measurement disc 10 in front of the examinee's eye. However, it is a cumbersome operation to prepare, store and exchange a plurality of the measurement discs 10, and is therefore undesirable. Furthermore, a refraction test is carried out on one eye at a time; however, there is a demand for the switching operation between the eyes being tested to be hassle free. Specifically, there is a demand for it to be unnecessary to replace the measurement disc 10 for the left and right eyes, to easily shield the eye that is not being tested, and to be able to easily perform measurements in a plurality of orientations with high precision. A measurement jig of the refraction measuring apparatus for solving the above-mentioned problems will be described in detail hereinafter.

Figure 5:
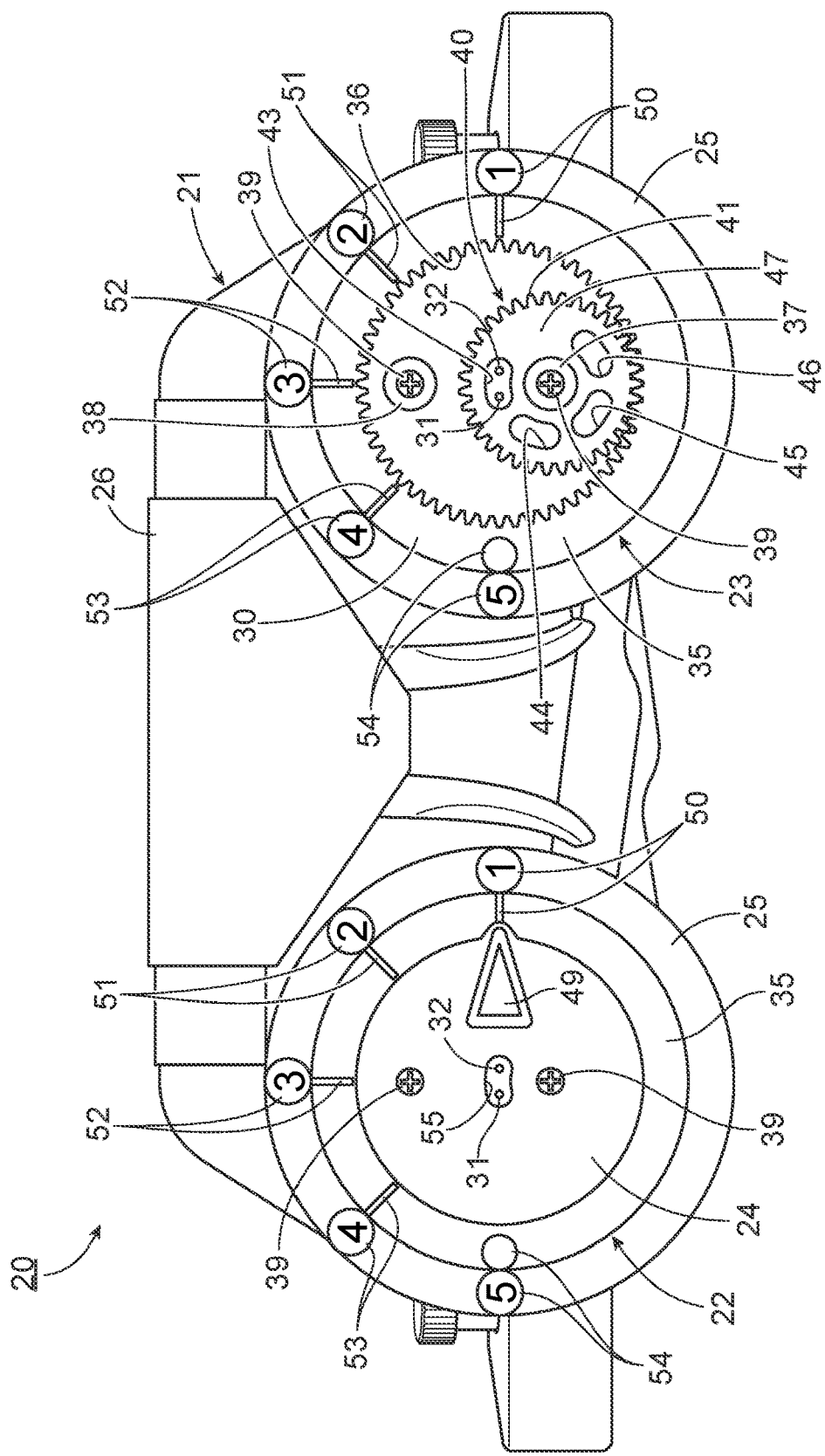
FIG. 5 shows a front elevational view of a measurement jig that forms the refraction measuring apparatus of the embodiment of the present invention.

A measurement jig 20 shown in FIG. 5 is provided with a holder member 21, having a structure resembling a spectacle frame (glasses frame); and two disc-units 22 and 23, according to a first embodiment, that are attached to (installed in) the holder member 21. The holder member 21 is a support member that directly or indirectly supports the members that form the respective structures of the disc units 22 and 23. The disc unit 22 is for testing the right eye and the disc unit 23 is for testing the left eye. The disc unit 22 and the disc unit 23 have the same structure (specifications), and parts that are common between the disc unit 22 and the disc unit 23 will be described only once. It should be noted that although FIG. 5 shows a cover 24 attached onto the disc unit 22 and a cover 24 not attached onto the disc unit 23, when the measurement jig 20 is actually in use, covers 24 are respectively attached onto both of the disc unit 22 and the disc unit 23.

The holder member 21 is provided with a pair of annular rims 25, which respectively support the disc unit 22 and the disc unit 23 and are mutually spaced apart in left and right directions. The pair of annular rims 25 are connected to each other by a bridge 26. Although details are omitted in this disclosure, an eye-width adjustment mechanism that adjusts the distance between the pair of annular rims 25 is provided on the bridge 26, and the disc unit 22 and the disc unit 23 can be appropriately (correctly) adjusted in front of the right eye and the left eye of the examinee, respectively. Furthermore, straps are provided in order to attach the holder member 21 to the examinee's head and face while adjusting the position of the holder member 21 relative thereto.

Details regarding the disc unit 22 and the disc unit 23 will be described hereinafter with reference to FIGS. 6 through 10. In each drawing from FIG. 6 onwards, the X-direction refers to the horizontal direction, and the Y-direction refers to the vertical direction. A measurement disc 30 is a round plate-shaped member corresponding to the measurement disc 10 of the refraction measuring apparatus of FIG. 1, and constitutes a first rotational member of the disc unit 22 (23). The measurement disc 30 is rotatable about a first rotational center P1 and is supported on a front surface of an annular rim 25 (of the pair of annular rims 25).

Furthermore, an inner gear member (annular gear) 35 is fixedly supported on a front side of the annular rim 25. The inner gear member 35 is provided with internal teeth 36 along an inner periphery of a cylindrical member that is centered about the first rotational center P1. The internal teeth 36 has an annular shape that is centered about the first rotational center P1. The measurement disc 30 is positioned between the annular rim 25 and the inner gear member 35 with respect to the forward/rearward direction.

A structure for rotationally supporting the measurement disc 30 can be provided in various forms. For example, an annular space may be provided between the annular rim 25 and the inner gear member 35, and a cylindrical guide surface, which is an inner peripheral surface of a cylindrical tube centered about the first rotational center P1, can define the outer peripheral portion of the annular space. The measurement disc 30 can be rotationally supported by the outer peripheral portion of the measurement disc 30 being in sliding contact with such a cylindrical guide surface.

As another example, an annular guide groove centered about the first rotational center P1 and opened in the forward/rearward direction may be formed in a front surface of the annular rim 25 or formed in a rear surface of the inner gear member 35, and the measurement disc 30 is rotatably supported by inserting a projection formed on the measurement disc 30 into the annular guide groove.

In either of the above-described example structures for rotationally supporting the measurement disc 30, forward and rearward movement of the measurement disc 30 is restricted due to the measurement disc 30 being sandwiched in between the annular rim 25 and the inner gear member 35, so that the measurement disc 30 can stably rotate. Furthermore, since the first light bundle L1 and the second light bundle L2 that are used for measurement pass near the center of the measurement disc 30 where the first rotational center P1 is located, the mechanism for supporting the measurement disc 30 rotatably so as not to block (shield) the first light L1 and the second light L2 is preferably provided at a peripheral edge portion of the measurement disc 30, rather than near the center of the measurement disc 30 in a radial direction.

The measurement disc 30 is provided with a first aperture 31 and a second aperture 32 that are formed at symmetrical positions on either side of the first rotational center P1. The first aperture 31 and the second aperture 32 are pinhole-shaped round apertures corresponding to the first aperture 11 and the second aperture 12 of FIG. 1. A direction extending along a straight line through the centers of the first aperture 31 and the second aperture 32, and through the first rotational center P1, define an aperture arrangement direction of the measurement disc 30. Furthermore, upon the measurement disc 30 being rotated, the angle of the aperture arrangement direction centered about the first rotational center P1 changes accordingly.

A shield control-plate 40 which forms a second rotational member in the disc unit 22 (23) is provided on a front side of the measurement disc 30. The shield control-plate 40 has a smaller diameter than that of the measurement disc 30, and is an external gear member provided with outer teeth 41 on the outer periphery thereof that internally meshes with the internal teeth 36.

The shield control-plate 40 is rotatably supported about a second rotational center P2 positioned eccentrically from the first rotational center P1 of the measurement disc 30. The second rotational center P2 is positioned on a straight line passing through the first rotational center P1 and extending orthogonally to the aperture arrangement direction. Specifically, a cylindrical shaft 37 projecting forward from the measurement disc 30 is inserted into a round-shaped shaft hole 42 provided in the shield control-plate 40, and the shield control-plate 40 rotates relative to the measurement disc 30 due to the inner peripherical surface of the shaft hole 42 being in sliding contact with the outer peripheral surface of the cylindrical shaft 37. Furthermore, the central positions of the cylindrical shaft 37 and the shaft hole 42 are the same as the second rotational center P2.

The internal teeth 36 of the inner gear member 35 and the outer teeth 41 of the shield control-plate 40 constitute a gear mechanism for rotating the shield control-plate 40 in association with the measurement disc 30, in which the shield control-plate 40 is rotated about the second rotational center P2 at a different angle of rotation to the unit angle-of-rotation of the measurement disc 30 that rotates about the first rotational center P1. The internal teeth 36 on the inner gear member 35 has a greater number of teeth than the outer teeth 41 of the shield control-plate 40, and the ratio thereof determined as 8:5. In the present aspect of the present disclosure, the internal teeth 36 is provided with sixty four (64) teeth, and the outer teeth 41 is provided with forty (40) teeth; however, these numbers of merely examples and may have different numbers of teeth.

The shield control-plate 40 is provided with four openings 43, 44, 45 and 46, which are formed at different positions in the rotational direction about the second rotational center P2. Furthermore, a region (section) of the shield control-plate 40 in the rotational direction between the opening 43 and the opening 46 defines a closed portion 47, which does not allow light to pass therethrough (does not have an opening). The openings 43, 44, 45 and 46 define light-transmission portions of the shield control-plate 40, and the closed portion 47 defines a light-shielding portion of the shield control-plate 40.

Each of the four openings 43, 44, 45 and 46 is an arc-shaped slot, the longitudinal direction thereof extending in the rotational direction about the second rotational center P2. The central positions relative to the longitudinal direction of the four openings 43, 44, 45 and 46 are positioned at 72-degree angles in the rotational direction about the second rotational center P2. Furthermore, the closed portion 47 is located at a position 72 degrees away from the respective central positions of the opening 43 and the opening 46, relative to the longitudinal directions thereof, in the forward and reverse rotational directions. Accordingly, five elements: the four openings, 43, 44, 45 and 46, and the closed portion 47, are arranged on the shield control-plate 40 at five equally-divided areas (72-degree sections), of a rotational angle of 360 degrees, about the second rotational center P2.

Five angular positional indicators 50, 51, 52, 53 and 54 are formed, at different positions in the rotational direction of the measurement disc 30 about the first rotational center P1, on a front surface of the annular rim 25 and the inner gear member 35. The angular positional indicators 50, 51, 52 and 53 are configured of respective combinations of linear marks, positioned on the front surface of the inner gear member 35 and extending in radial directions about the first rotational center P1, and circled numbers from "1" through "4", positioned on the front surface of the annular rim 25. The remaining angular positional indicator 54 is configured of a combination of a circular mark, positioned on the front surface of the inner gear member 35, and a circled number "5", positioned on the front surface of the annular rim 25.

The five angular positional indicators 50, 51, 52, 53 and 54 are arranged at 45-degree equi-angular intervals in the rotational direction about the first rotational center P1. In other words, the five angular positional indicators 50, 51, 52, 53 and 54 are arranged at four equi-divided positions, of a 180-degree rotational angle, of the measurement disc 30 about the first rotational center P1. The circular mark and the linear marks provided on the front surface of the inner gear member 35 are used as positional references, in the rotational direction, for the angular positional indicators 50, 51, 52, 53 and 54. In other words, the positions of the circled numbers "1" to "5" positioned on the front surface of the annular rim 25 may be slightly shifted out of alignment in the rotational direction providing that the circled numbers "1" to "5" are within ranges so that the corresponding relationships thereof with the circular mark and the linear marks can be identified.

The covers 24 (refer to FIG. 5) which cover the front of the measurement disc 30 and the shield control-plate 40 are attached onto the disc unit 22 and the disc unit 23, respectively. Each cover 24 has a round plate shape, and the outer diameter size of each cover 24 is determined slightly larger than the inner diameter of the inner gear member 35. Accordingly, when each cover 24 is attached, the internal teeth 36 and the internal area thereof cannot be visually confirmed from the outside. An area on the front surface of the inner gear member 35, except for the internal teeth 36, is not covered by the cover 24 and is externally visible; the circular mark and the linear marks of the angular positional indicators 50, 51, 52, 53 and 54 are arranged on this externally visible area.

The measurement disc 30 is provided, separately from the cylindrical shaft 37 that rotationally supports the shield control-plate 40, with a cylindrical shaft 38 which projects in the forward direction. The cylindrical shaft 38 is provided at an opposite side of the first rotational center P1 from the cylindrical shaft 37, relative to the radial direction of the measurement disc 30. The position of the cover 24 in the forward/rearward direction is determined by the front-end faces of the cylindrical shaft 37 and the cylindrical shaft 38 abutting against the cover 24.

The cover 24 is provided with two through-holes respectively corresponding to the cylindrical shaft 37 and the cylindrical shaft 38, and fastening members (e.g., fastening screws) 39 are respectively inserted (or screwed) into the cylindrical shaft 37 and the cylindrical shaft 38 via the two through-holes. Female threads are formed inside the cylindrical shaft 37 and the cylindrical shaft 38, respectively, and male threads are formed on the outer surfaces of the fastening members 39, respectively. Accordingly, the cover 24 is fixed to the measurement disc 30 by screw-engaging the female threads with the male threads and fastening the fastening members 39 with an appropriate amount of torque. In this fastened state, upon a force in a rotational direction being applied on the cover 24 (upon a rotational operation being performed), the cover 24 and the measurement disc 30 integrally rotate about the first rotational center P1.

An exposure hole 55 is formed through the center of the cover 24. The exposure hole 55 is in the form of a slot having a longitudinal direction in the aperture arrangement direction of the measurement disc 30. The first aperture 31 and the second aperture 32 are exposed through the exposure hole 55 in a forward direction of the cover 24 (refer to FIG. 5). Since the cover 24 and the measurement disc 30 are integrated in a rotational direction about the first rotational center P1, the first aperture 31 and the second aperture 32 are always exposed through the exposure hole 55 regardless of the angular position of the measurement disc 30 in the rotational direction.

In addition, a marker 49 is formed on the cover 24. The marker 49 is an arrow-shaped (triangular-shaped) marker extending in a longitudinal direction of the exposure hole 55 and points toward an outer radial direction (pointing away from the exposure hole 55) of the cover 24.

When the measurement jig 20 is fitted onto (worn by) the examinee, the respective first rotational centers P1 (the central position between the first aperture 31 and the second aperture 32) of the left and right disc units 22 and 23 are set to (aligned with) positions on extensions of the respective axes of vision Q (FIG. 1) of the left and right eyes of the examinee. Thereafter, by performing a rotational operation of the cover 24 and the measurement disc 30 in the disc units 22 and 23, each having the above-described structure, the refractive properties of the eye can be measured at a plurality of orientations while shielding the opposite eye (the other eye of the examinee) that is not being tested.

Hereinbelow, a description will be given regarding the measurement of the refractive properties of the eye using the disc units 22 and 23. It should be noted that when changing the measuring direction by changing the angular position of the measurement disc 30 in each of the disc units 22 and 23, the angular positions of the visual marker 14 and the visual marker 15 in the light-emission device 13 (FIG. 1) change correspondingly, so that the aperture arrangement direction of the measurement disc 30 and the arrangement direction of the visual markers 14 and 15 are always in an associated relationship.

For example, if the examinee or the person conducting the measurement manually changes the angular position of the measurement disc 30 relative to the disc unit 22 (23), the changed angular-position information is input into the processor 16 (FIG. 1) via an input device (such as a keyboard, touch panel, etc.). Thereupon, the processor 16 controls the light-emission device 13 to change the angular position of the visual marker 14 and the visual marker 15.

Alternatively, an observing device (e.g., a camera), may be provided in the refraction measuring apparatus, which can detect the orientation (direction) of the marker 49 by imaging (photographing) the disc unit 22 (23) and utilizing image analysis technology. Accordingly, the processor 16 automatically controls the light-emission device 13 based on the position of the cover 24 detected by the observing device to change the angular position of the visual markers 14 and the visual marker 15.

Furthermore, by using such an observing device, it is possible to also check (confirm) the position at which the measurement jig 20 is set. For example, when examining the right eye, it can be detected when the disc unit 23 for the left eye is not at a light-shielding position (or vice versa). In such a case, the processor 16 may alert the examinee or the person conducting the measurement that an error has occurred.

Figure 6:
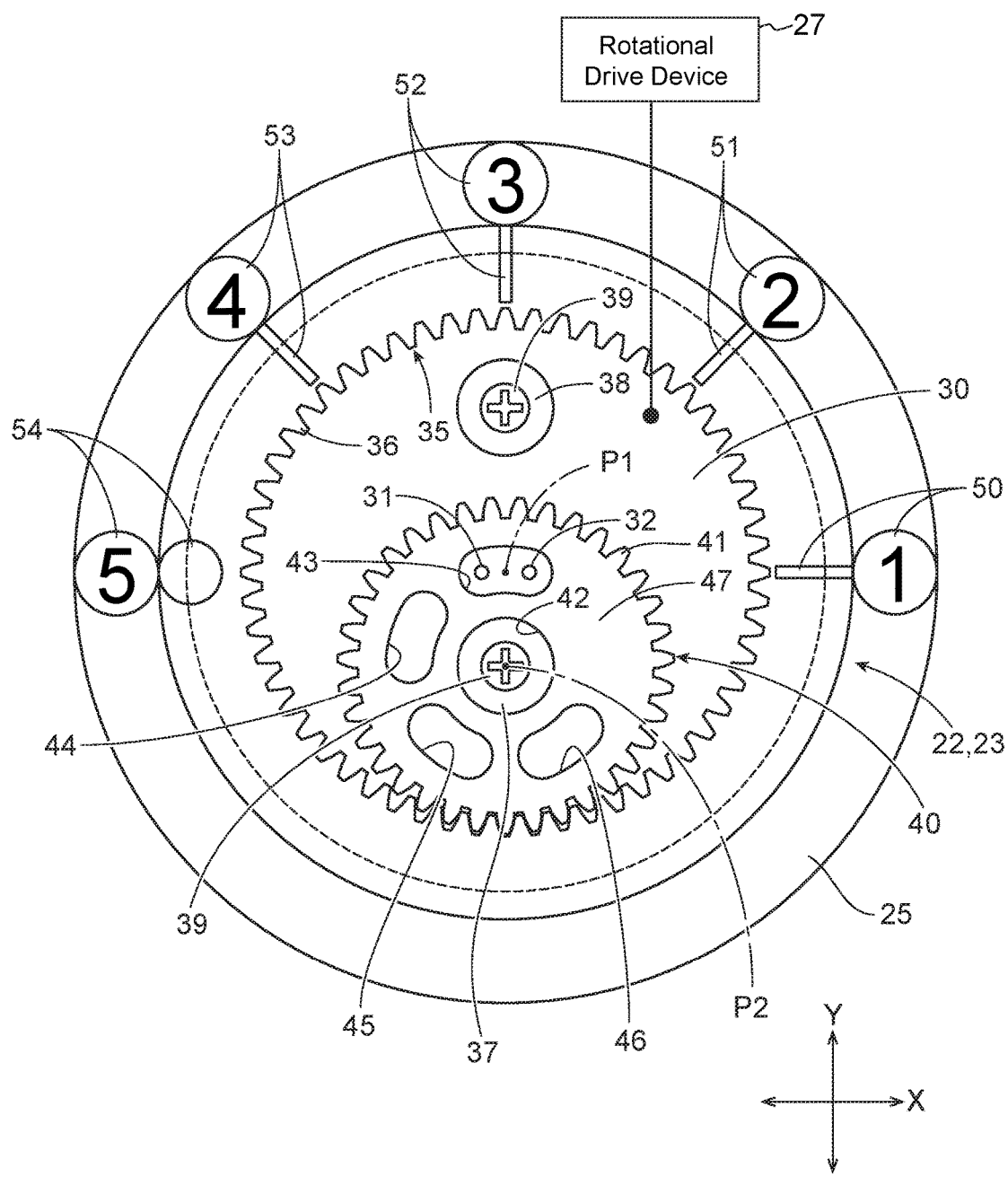
FIG. 6 shows an internal structure of a disc unit, of a first embodiment, at a first angular position.

FIG. 6 shows the internal structure of the disc unit 22 (and the disc unit 23) in a state (shown in FIG. 5) where the end of the marker 49 on the cover 24 points to the first angular position indicating the angular positional indicator 50. In this state, the central axis of the cylindrical shaft 37 (second rotational center P2), the central axis of the cylindrical shaft 38 and the first rotational center P1 are arranged along a straight line in the Y-direction. Furthermore, the aperture arrangement direction of the first aperture 31 and the second aperture 32 of the measurement disc 30 align in the X-direction. The shield control-plate 40 is in mesh with the inner gear member 35 via the outer teeth 41 being mesh with the internal teeth 36 at the lowest area of the inner gear member 35 relative to the Y-direction, and the first aperture 31 and the second aperture 32 are positioned within (coincide within) the opening 43 in a front elevation view. In other words, the disc unit 22 (23) is in a state in which the first light bundle L1 and the second light bundle L2 (refer to FIG. 1) can pass through the first aperture 31 and the second aperture 32 via (through) the opening 43.

Accordingly, by setting the disc unit 22 and the disc unit 23 to the state (the first angular position) shown in FIG. 6, the first light bundle L1 and the second light bundle L2 can pass through the exposure hole 55 of the cover 24 and the opening 43 of the shield control-plate 40 to pass through the first aperture 31 and the second aperture 32. Thereafter, based on the image (the visual marker images 14M and 15M) formed on the retina by the first light bundle L1 and the second light bundle L2 passing through the first aperture 31 and the second aperture 32, respectively, the refractive properties of the eye can be measured in the orientation of the X-direction (horizontal direction), which corresponds to the aperture arrangement direction of the first aperture 31 and the second aperture 32. In this state, since the linear marker of the angular positional indicator 50, to which the marker 49 points, extends in the aperture arrangement direction, the orientation of the refraction measurement can be easily visually identified.

Figure 7:
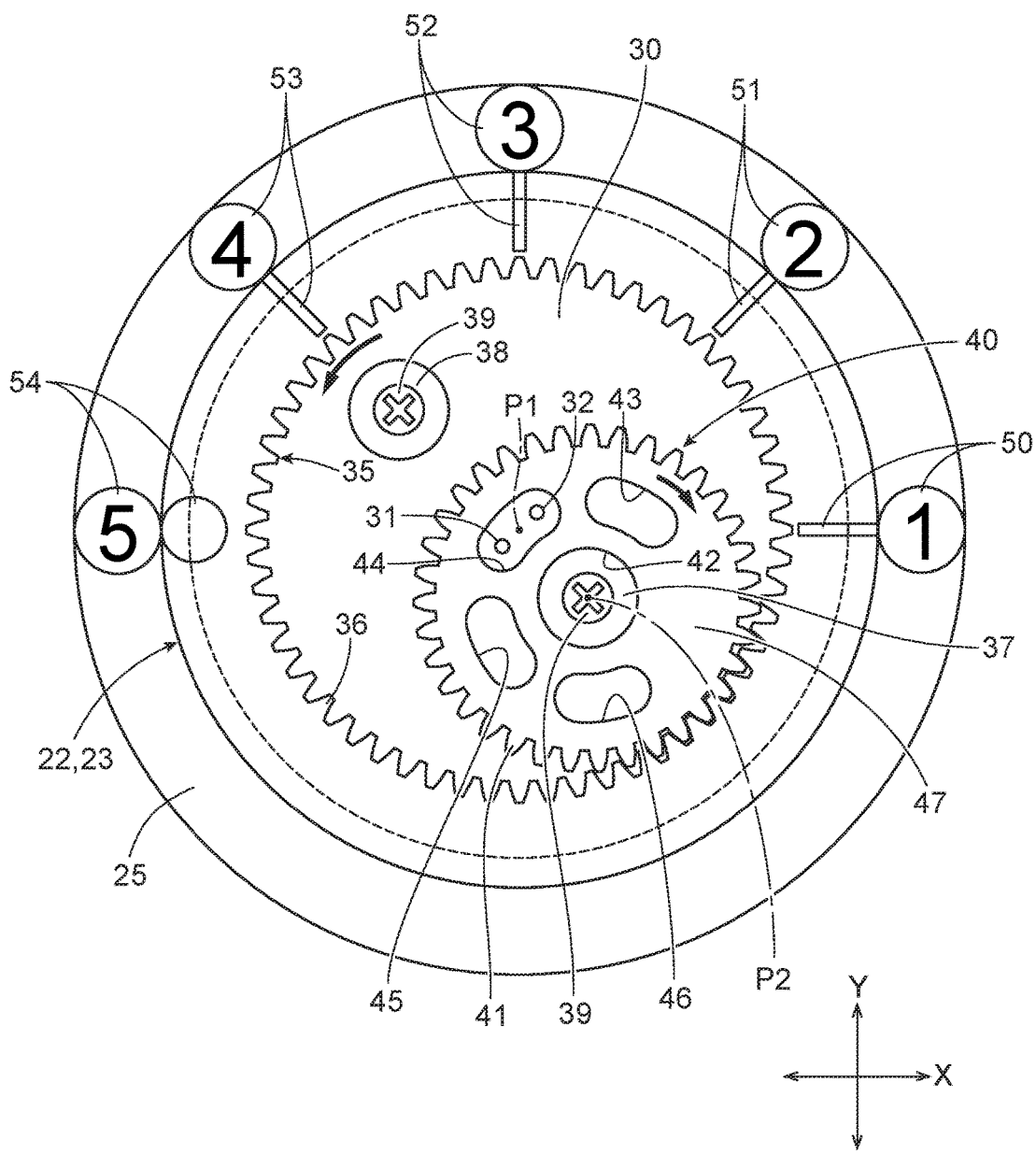
FIG. 7 shows the internal structure of the disc unit, of the first embodiment, at a second angular position.

FIG. 7 shows the internal structure of the disc unit 22 (and the disc unit 23) in a state where the end of the marker 49 on the cover 24 points to the second angular position indicating the angular positional indicator 51. The measurement disc 30 is rotated 45 degrees anti-clockwise about the first rotational center P1 from the first angular position shown in FIG. 6, in a front elevation view, so that the aperture arrangement direction of the first aperture 31 and the second aperture 32 inclines 45 degrees upward, toward the right side, relative to the X-direction.

Upon the measurement disc 30 being rotated about the first rotational center P1, the shield control-plate 40, which is supported by the measurement disc 30 via the cylindrical shaft 37 and the shaft hole 42, also rotates (moves in the rotational direction about the first rotational center P1) with the measurement disc 30. Thereupon, the shield control-plate 40 rotates (planetary rotation) about the second rotational center P2 while changing the meshing position of the outer teeth 41 (of the shield control-plate 40) relative to the internal teeth 36 (of the inner gear member 35). In this state the measurement disc 30 advances in the anti-clockwise direction about the first rotational center P1, whereas the shield control-plate 40 rotates in the clockwise direction about the second rotational center P2.

As a result of the operation of the shield control-plate 40 (the combined operation of the positional change of the second rotational center P2 occurring about the first rotational center P1, and the planetary rotation about the second rotational center P2), the opening 44 is positioned in front of the first aperture 31 and the second aperture 32 in a state where the longitudinal direction of the opening 44 inclines 45 degrees upward, toward the right side, relative to the X-direction. In other words, the first aperture 31 and the second aperture 32 are positioned within the opening 44 in a front elevation view, and the first light bundle L1 and the second light bundle L2 (refer to FIG. 1) can pass through the first aperture 31 and the second aperture 32 via (through) the opening 44.

Accordingly, by setting the disc unit 22 and the disc unit 23 to the state (the second angular position) shown in FIG. 7, the first light bundle L1 and the second light bundle L2 can pass through the exposure hole 55 of the cover 24 and the opening 44 of the shield control-plate 40 to pass through the first aperture 31 and the second aperture 32. Thereafter, based on the image (the visual marker images 14M and 15M) formed on the retina by the first light bundle L1 and the second light bundle L2 passing through the first aperture 31 and the second aperture 32, respectively, the refractive properties of the eye can be measured at a first intermediate orientation between the X-direction (horizontal direction) and the Y-direction (vertical direction), which corresponds to the aperture arrangement direction of the first aperture 31 and the second aperture 32. In this state, since the linear marker of the angular positional indicator 51, to which the marker 49 points, extends in the aperture arrangement direction, the orientation of the refraction measurement can be easily visually identified.

Figure 8:
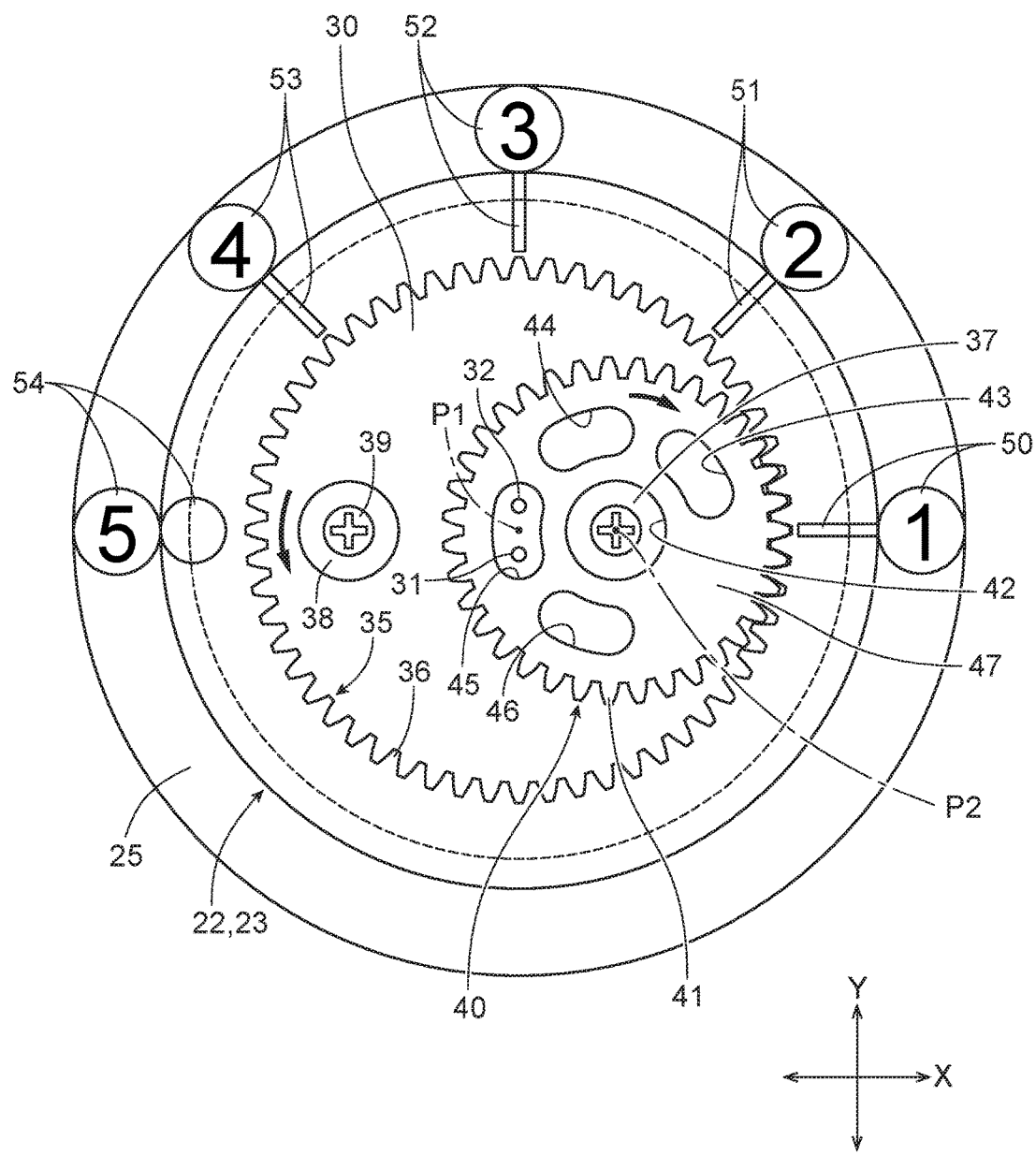
FIG. 8 shows the internal structure of the disc unit, of the first embodiment, at a third angular position.

FIG. 8 shows the internal structure of the disc unit 22 (and the disc unit 23) in a state where the end of the marker 49 on the cover 24 points to the third angular position indicating the angular positional indicator 52. The measurement disc 30 is rotated 45 degrees anti-clockwise about the first rotational center P1 from the second angular position shown in FIG. 7, in a front elevation view, so that the aperture arrangement direction of the first aperture 31 and the second aperture 32 extends along the Y-direction.

Due to the rotation of the measurement disc 30 from the second angular position to the third angular position, the shield control-plate 40 rotates (planetary rotation) about the second rotational center P2 while changing the meshing position of the outer teeth 41 (of the shield control-plate 40) relative to the internal teeth 36 (of the inner gear member 35).

As a result of this operation of the shield control-plate 40, the opening 45 is positioned in front of the first aperture 31 and the second aperture 32 in a state where the longitudinal direction of the opening 45 extends in the Y-direction. In other words, the first aperture 31 and the second aperture 32 are positioned within the opening 45 in a front elevation view, and the first light bundle L1 and the second light bundle L2 (refer to FIG. 1) can pass through the first aperture 31 and the second aperture 32 via (through) the opening 45.

Accordingly, by setting the disc unit 22 and the disc unit 23 to the state (the third angular position) shown in FIG. 8, the first light bundle L1 and the second light bundle L2 can pass through the exposure hole 55 of the cover 24 and the opening 45 of the shield control-plate 40 to pass through the first aperture 31 and the second aperture 32. Thereafter, based on the image (the visual marker images 14M and 15M) formed on the retina by the first light bundle L1 and the second light bundle L2 passing through the first aperture 31 and the second aperture 32, respectively, the refractive properties of the eye can be measured in the Y-direction (vertical direction), which corresponds to the aperture arrangement direction of the first aperture 31 and the second aperture 32. In this state, since the linear marker of the angular positional indicator 52, to which the marker 49 points, extends in the aperture arrangement direction, the orientation of the refraction measurement can be easily visually identified.

Figure 9:
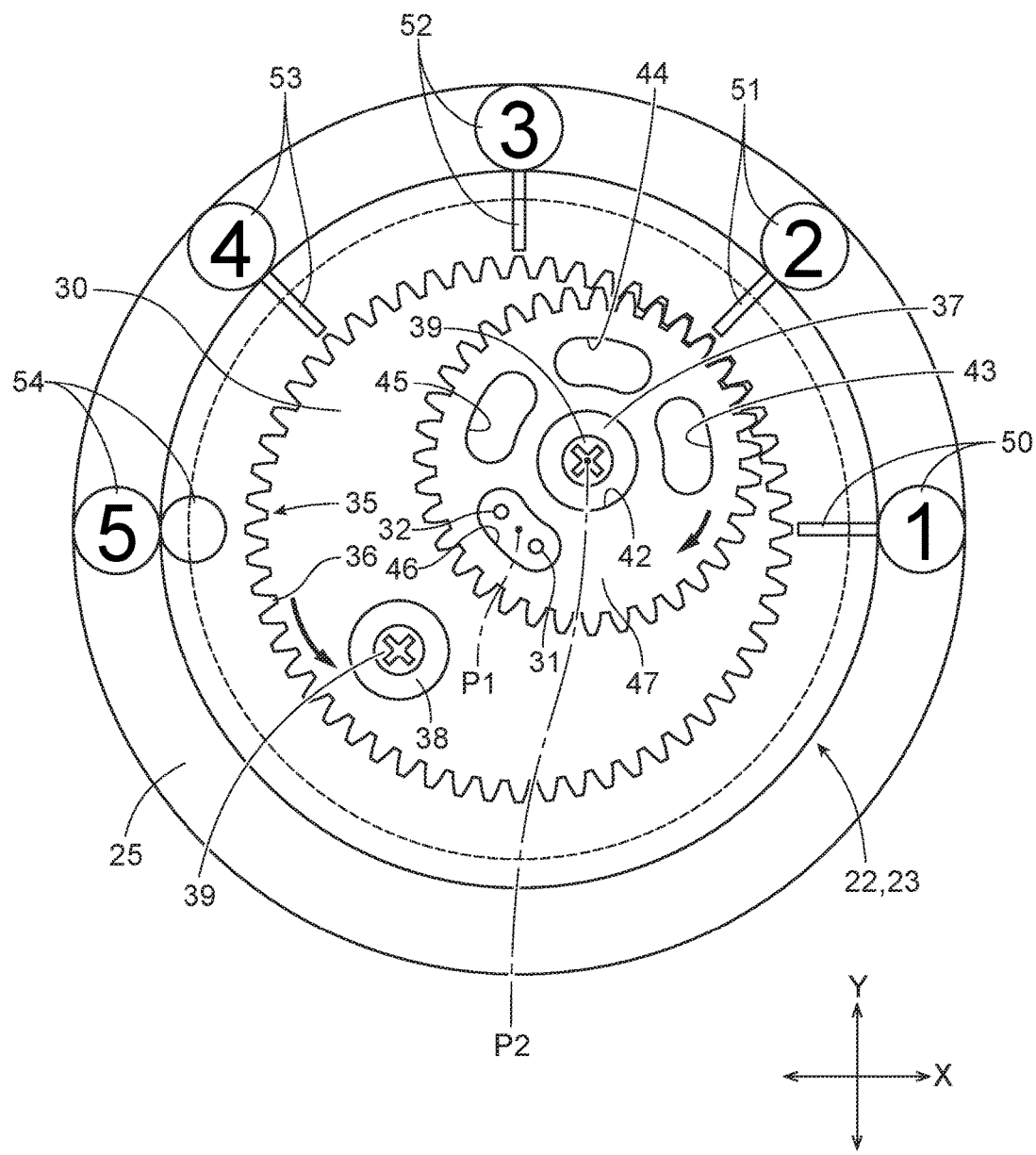
FIG. 9 shows the internal structure of the disc unit, of the first embodiment, at a fourth angular position.

FIG. 9 shows the internal structure of the disc unit 22 (and the disc unit 23) in a state where the end of the marker 49 on the cover 24 points to the fourth angular position indicating the angular positional indicator 53. The measurement disc 30 is rotated 45 degrees anti-clockwise about the first rotational center P1 from the third angular position shown in FIG. 8, in a front elevation view, so that the aperture arrangement direction of the first aperture 31 and the second aperture 32 inclines 45 degrees downward, toward the right side, relative to the X-direction. This aperture arrangement direction is inverted right-to-left relative to the aperture arrangement direction of the second angular position shown in FIG. 7, and has changed by 135 degrees relative to the aperture arrangement direction, when set to 0 degrees, of the first angular position shown in FIG. 6.

Due to the rotation of the measurement disc 30 from the third angular position to the fourth angular position, the shield control-plate 40 rotates (planetary rotation) about the second rotational center P2 while changing the meshing position of the outer teeth 41 (of the shield control-plate 40) relative to the internal teeth 36 (of the inner gear member 35).

As a result of this operation of the shield control-plate 40, the opening 46 is positioned in front of the first aperture 31 and the second aperture 32 in a state where the longitudinal direction of the opening 46 inclines 45 degrees (135 degrees with reference to the first angular position) downward, toward the right side, relative to the X-direction. In other words, the first aperture 31 and the second aperture 32 are positioned within the opening 46 in a front elevation view, and the first light bundle L1 and the second light bundle L2 (refer to FIG. 1) can pass through the first aperture 31 and the second aperture 32 via (through) the opening 46.

Accordingly, by setting the disc unit 22 and the disc unit 23 to the state (the fourth angular position) shown in FIG. 9, the first light bundle L1 and the second light bundle L2 can pass through the exposure hole 55 of the cover 24 and the opening 46 of the shield control-plate 40 to be pass through the first aperture 31 and the second aperture 32. Thereafter, based on the image (the visual marker images 14M and 15M) formed on the retina by the first light bundle L1 and the second light bundle L2 passing through the first aperture 31 and the second aperture 32, respectively, the refractive properties of the eye can be measured at a second intermediate orientation (135-degree direction) between the X-direction (horizontal direction) and the Y-direction (vertical direction), which corresponds to the aperture arrangement direction of the first aperture 31 and the second aperture 32. In this state, since the linear marker of the angular positional indicator 53, to which the marker 49 points, extends in the aperture arrangement direction, the orientation of the refraction measurement can be easily visually identified.

Figure 10:
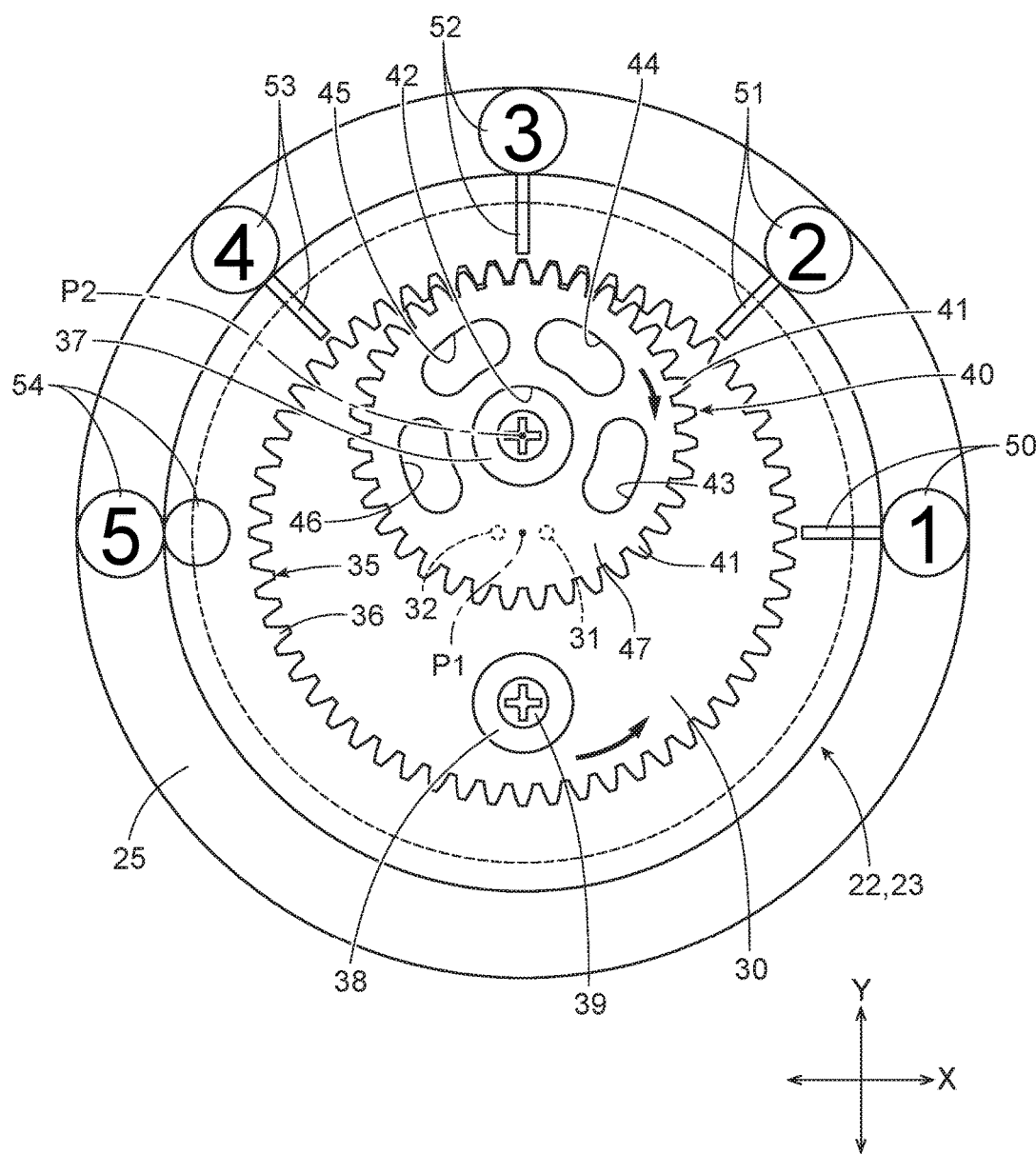
FIG. 10 shows the internal structure of the disc unit, of the first embodiment, at a fifth angular position.

FIG. 10 shows the internal structure of the disc unit 22 (and the disc unit 23) in a state where the end of the marker 49 on the cover 24 points to the fifth angular position indicating the angular positional indicator 54. The measurement disc 30 is rotated 45 degrees anti-clockwise about the first rotational center P1 from the fourth angular position shown in FIG. 9, in a front elevation view, so that the aperture arrangement direction of the first aperture 31 and the second aperture 32 extends in the X-direction. In this state, the positional relationship of the first aperture 31 and the second aperture 32 is reversed right-to-left relative to the positional relationship of the first aperture 31 and the second aperture 32 in the first angular position shown in FIG. 6.

Due to the rotation of the measurement disc 30 from the fourth angular position to the fifth angular position, the shield control-plate 40 rotates (planetary rotation) about the second rotational center P2 while changing the meshing position of the outer teeth 41 (of the shield control-plate 40) relative to the internal teeth 36 (of the inner gear member 35).

As a result of this operation of the shield control-plate 40, the closed portion 47 is positioned in front of the first aperture 31 and the second aperture 32 so that the first light bundle L1 and the second light bundle L2 (refer to FIG. 1) that emanate toward the first aperture 31 and the second aperture 32 are shielded by the closed portion 47.

Accordingly, by setting the disc unit 22 and the disc unit 23 to the state (the fifth angular position) shown in FIG. 10, the first aperture 31 and the second aperture 32 are shielded by the closed portion 47 of the shield control-plate 40, so that the first light bundle L1 and the second light bundle L2 cannot pass through the shield control-plate 40. In this state, since the angular positional indicator 54, to which the marker 49 points, is a circular marker, which differs from the other angular positional indicators 50, 51, 52 and 53, the state in which the measurement of the refractive properties of the eye is not performed (a light-shielded state) at a specified orientation can be visually identified easily.

As described above, in the disc unit 22 and the disc unit 23, the orientation of a measurement of the refractive properties of the eye can be changed (switched) between a plurality of orientations, and the first and second apertures 31 and 32 can be switched to a light-shielding state (from a light transmission state) by a desired angular position being selected out of first through fifth angular positions by operating the cover 24.

As a specific example of using the measurement jig 20, the cover 24 and the measurement disc 30 may be set to the fifth angular position (FIG. 10) in the disc unit 23 for the left eye, and the cover 24 and the measurement disc 30 may be successively changed from the first angular position (FIG. 6) until the fourth angular position (FIG. 9) in the disc unit 22 for the right eye to thereby measure the refractive properties of the right eye at each orientation. By setting the cover 24 and the measurement disc 30 to the fifth angular position in the disc unit 23 for the left eye, unwanted light can be prevented from entering left eye during the refraction test of the right eye.

Upon completion of the refraction test of the right eye, the cover 24 and the measurement disc 30 are set to the fifth angular position (FIG. 10) in the disc unit 22 for the right eye. Thereafter, the cover 24 and the measurement disc 30 are successively changed from the first angular position (FIG. 6) until the fourth angular position (FIG. 9) in the disc unit 23 for the left eye to thereby measure the refractive properties of the left eye at each orientation. By setting the cover 24 and the measurement disc 30 to the fifth angular position in the disc unit 22 for the right eye, unwanted light can be prevented from entering right eye during the refraction test of the left eye.

In the above-described measurement jig 20, the disc unit 22 for the right eye and the disc unit 23 for the left eye are separately provided for use, and since there is no replacing or exchanging of components when changing to one eye to the other for testing, there is no need to perform an operation in which components are removed and attached (replaced/exchanged). Furthermore, in each of the disc unit 22 and the disc unit 23, since the all of the operations of selecting the orientations for measuring the refractive properties and setting a shielded state are performed by using only the integral rotating operation (of selecting an angular position) of the cover 24 and measurement disc 30, the workability of the measurement jig 20 is superior compared to an apparatus that requires a plurality of different operations. Since the angular position of the measurement disc 30 is distinguished by referring to the positional relationship between the marker 49 and the angular positional indicators 50, 51, 52, 53 and 54, the measurement disc 30 can be set to an appropriate angular position to perform a high-precision examination.

In the disc units 22 and 23, since the refractive properties of each eye can be measured at four orientations, i.e., a horizontal direction (X-direction), a vertical direction (Y-direction), and two intermediate orientations therebetween (45-degree and 135-degree directions), a high-precision examination can be carried out. Furthermore, the ratio of the number of teeth of the internal teeth 36 on the inner gear member 35 to the outer teeth 41 of the shield control-plate 40 is set to 8:5 in order to achieve a light-transmission state at four different orientations (directions), and a light-shielding state at an angular position that is different to the other four orientations.

Furthermore, in the disc unit 22 and the disc unit 23, the cover 24 and the gear mechanism (inner gear member 35), etc., associated with rotationally driving and supporting the measurement disc 30 and the shield control-plate 40 are arranged so that such components are accommodated inside the annular rim 25 of the holder member 21 in a front elevational view. Accordingly, the measurement jig 20 can achieve a compact structure.

Furthermore, by using the disc units 22 and 23, which have the same structure, for the right eye and for the left eye, respectively, the number of components can be reduced, thereby reducing manufacturing costs.

It should be noted that various types of devices may be used for applying a rotational force on the measurement disc 30 and the shield control-plate 40. The above-described embodiment assumes that a manual operation is performed by the examinee or the person conducting the measurement, so that force is transferred to the measurement disc 30 and the shield control-plate 40 in accordance with an external (manual) force applied on the rotationally operable cover 24. Such an embodiment has the advantages of not requiring a drive source and being able to achieve a simple power transmission structure. Furthermore, due to the cover 24, which that covers the internal structure of the disc unit 22 and the disc unit 23, also having the role of an input member for the rotational operation, the component structure for performing the rotational operation can be simplified.

However, it is possible to use a rotational drive device 27 (FIG. 6) having a drive source such as a motor, etc., to rotate the measurement disc 30. As mentioned above, in each disc unit 22 and 23, since the all of the operations of selecting the measurement orientations and setting a shielded state are performed only by the rotating operation measurement disc 30 (integrally with the cover 24), a simple in structure and low-cost rotational drive device 27 can be used.

Furthermore, in the case where the measurement disc 30 is rotated manually, an externally-operable lever may be provided and connected to the measurement disc 30, part of an outer peripheral portion of the measurement disc 30 may be exposed in order to be externally operated, or the measurement disc 30 may be rotated via an operation on a part other than the cover 24.

Furthermore, the measurement disc 30 may be provided with a structure that stops (holds) at a plurality of angular positions in the rotational direction. For example, a click mechanism may be provided between the holder member 21 and the measurement disc 30, and the rotation of the measurement disc 30 can be mechanically and softly engaged (with tactile feedback) at each of the above-described first through fifth angular positions. Upon applying a force in the rotational direction that exceeds a certain amount of force, the engagement state of the click mechanism releases, allowing the measurement disc 30 to rotate and arrive at a subsequent angular position. Providing such a click mechanism enables a measurement orientation or a shielded state to be accurately and easily set, thereby improving workability and precision of the examination (refraction test).

Furthermore, in order to prevent a positional shift in the rotational direction of the measurement disc 30 and in order to optimize the rotation operational force, a friction device, etc., may be provided, between the holder member 21 and the measurement disc 30, to apply a predetermined rotational load on the measurement disc 30.

It should be noted that if the measurement disc 30 is rotated in the same direction by a rotation angle greater than 360 degrees, the positional relationships at the first through fifth angular positions from the second (360-degree) rotation onwards between the first and second apertures 31 and 32 of the measurement disc 30, and the openings 43, 44, 45, 46, and the closed portion 47 of the shield control-plate 40, will no longer satisfy the positional relationships indicated in FIGS. 6 through 10. Accordingly, a stopper mechanism may be provided that restricts the maximum rotational angle to 360 degrees or less. Furthermore, as shown in FIGS. 6 through 10, since the total rotational angle of the measurement disc 30 from the first angular position to the fifth angular position amounts to 180 degrees, the stopper mechanism may restrict the maximum rotation of the measurement disc 30 to 180 degrees.

FIGS. 11 through 15 show modified embodiments of the shield control-plate 40, constituting part of the disc unit 22 (23) of the first embodiment, having different light-transmission portion configurations. In each of these modified embodiments, duplicate descriptions of parts and components, already described above, indicated with the same reference designators and having the same structures have been omitted.

Figure 11:
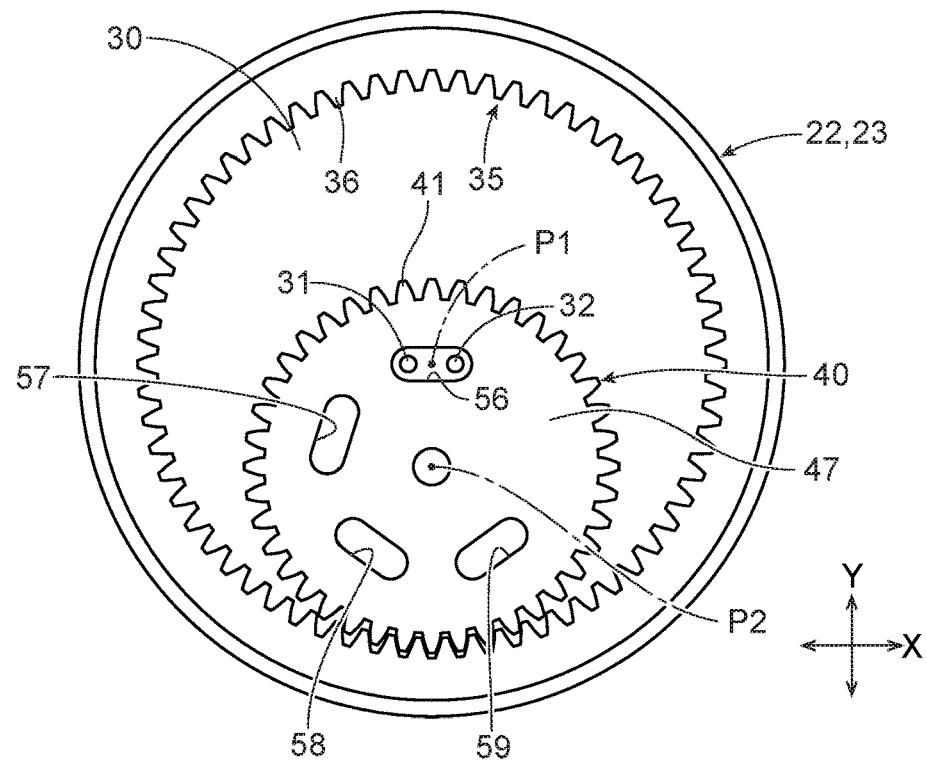
FIG. 11 shows a modified embodiment of the disc unit of the first embodiment.

In the modified embodiment shown in FIG. 11, each of four openings (light-transmission portions) 56, 57, 58 and 59 formed in (through) the shield control-plate 40 is not an arc-shaped slot centered about the second rotational center P2, but rather is a straight linear slot. Furthermore, each of the openings 56, 57, 58 and 59 extends along a tangent direction that is tangent to an imaginary circle centered about the second rotational center P2.

At the above-mentioned first angular position of the measurement disc 30 (the state shown in FIG. 11), the opening 56 coincides with the first aperture 31 and the second aperture 32 (so that the first aperture 31 and the second aperture 32 coincide within the opening 56). Similarly, the openings 57 through 59 coincide with the first and second apertures 31 and 32 at respective above-mentioned second through fourth angular positions (FIG. 6 through FIG. 9) of the measurement disc 30. Accordingly, at each of these four angular positions, the first light bundle L1 and the second light bundle L2 (refer to FIG. 1) pass through the first aperture 31 and the second aperture 32, so that the refractive properties of the eye can be measured at each orientation. Furthermore, at the above-mentioned fifth angular position of the measurement disc 30 (FIG. 10), a closed portion 47 provided between the opening 56 and the opening 59 coincide with the first aperture 31 and the second aperture 32, and shield (block) the transmission of the first light bundle L1 and the second light bundle L2.

Figure 12:
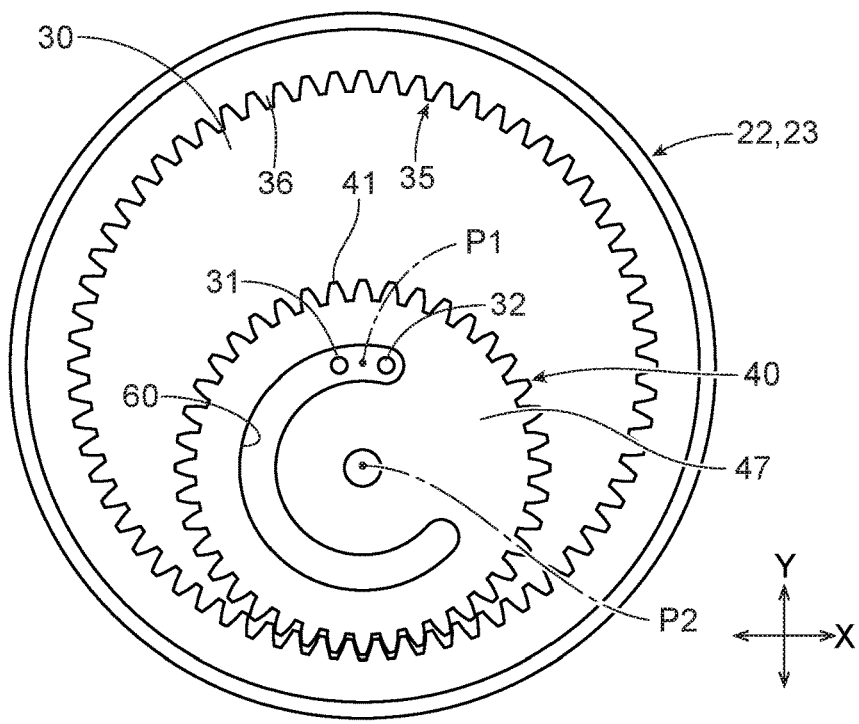
FIG. 12 shows another modified embodiment of the disc unit of the first embodiment.

In the modified embodiment shown in FIG. 12, a light-transmission portion is formed by a continuous opening 60 that is continuous in the rotational direction about the second rotational center P2. For example, by mutually connecting longitudinally end-portions that correspond to the ends of the openings 43 through 46 of the first embodiment, a long arc-shaped continuous opening 60 can be formed without being divided (discontinuous) in the rotational direction.

Figure 13:
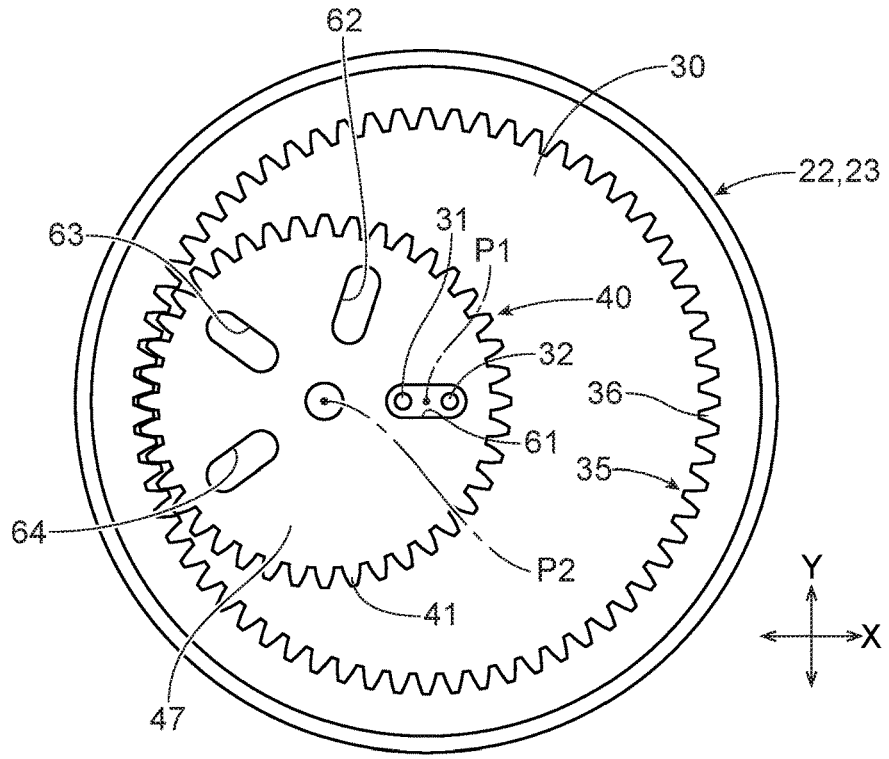
FIG. 13 shows another modified embodiment of the disc unit of the first embodiment.

In the modified embodiment shown in FIG. 13, light-transmission portions are formed by four openings 61, 62, 63 and 64 formed in (through) the shield control-plate 40 so that each longitudinal direction thereof extends in a radial direction from the second rotational center P2. The longitudinal direction of each of the four openings 61, 62, 63 and 64 extends in the aperture arrangement direction at the above-mentioned first through fourth angular positions to coincide with the first aperture 31 and the second aperture 32, and function in the same manner as the above-described openings 43, 44, 45 and 46.

In the configuration shown in FIG. 11, the second rotational center P2 is positioned on a straight line that is orthogonal to the aperture arrangement direction of the first aperture 31 and the second aperture 32. Correspondingly, the longitudinal direction of each of the openings 56, 57, 58 and 59 extend in a direction orthogonal to the radial direction from the second rotational center P2. Whereas, in the configuration shown in FIG. 13, the second rotational center P2 is positioned on an extension (straight line) in the aperture arrangement direction of the first aperture 31 and the second aperture 32. Correspondingly, the longitudinal direction of each of the openings 61, 62, 63 and 64 extends in the radial direction from the second rotational center P2. Accordingly, the orientations of plurality of openings provided in the shield control-plate 40 differ depending on the position of the second rotational center P2 relative to the aperture arrangement direction of the measurement disc 30.

It should be noted that in the modified embodiment of FIG. 13, the meshing positions of the outer teeth 41 with the internal teeth 36 differ from those of the embodiments shown in FIGS. 6 through 12 due to the difference in the shape (in the longitudinal direction) of the openings 61, 62, 63 and 64. Specifically, in the embodiments shown in FIGS. 6 through 12, at the first angular position (FIGS. 6, 11 and 12) in which the refractive properties are measured in the horizontal direction, the outer teeth 41 is meshed with the internal teeth 36 at an end (lower end) of the inner gear member 35 in the Y-direction. Whereas, in the first angular position shown in FIG. 13, the outer teeth 41 is meshed with the internal teeth 36 at an end of the inner gear member 35 in the X-direction.

Figure 14:
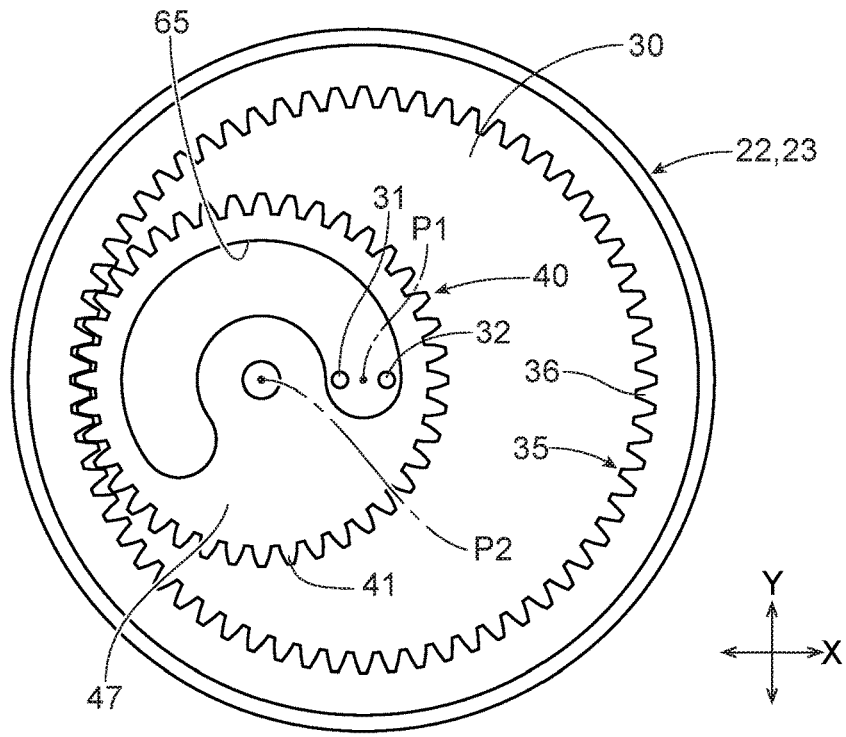
FIG. 14 shows another modified embodiment of the disc unit of the first embodiment.

In the modified embodiment shown in FIG. 14, a light-transmission portion is formed by a continuous opening 65 that is continuous in the rotational direction about the second rotational center P2. The continuous opening 65 is formed as a long arc-shaped opening (slot) that is continuous in the rotational direction (without being divided or discontinuous) in a manner such that side portions, extending in the radial direction of the shield control-plate 40, of portions corresponding to the openings 61 through 64 in FIG. 13, are mutually connected.

If an opening having a shape that is continuous in the rotational direction (like the continuous opening 60 of FIG. 12 or the continuous opening 65 of FIG. 14) is used, it is possible for the first light bundle L1 and the second light bundle L2 to pass through the first aperture 31 and the second aperture 32 at not only the first through fourth angular positions, but also at intermediate angular positions between the first through fourth angular positions. In other words, in a light-transmission state, the first light bundle L1 and the second light bundle L2 can pass (through the first aperture 31 and the second aperture 32) while continuously changing the aperture arrangement direction of the first aperture 31 and the second aperture 32 within the range defined by the continuous opening 60 or the continuous opening 65. According to such a structure, the refractive properties of the eye can be measured at a large variety of orientations.

Figure 15:
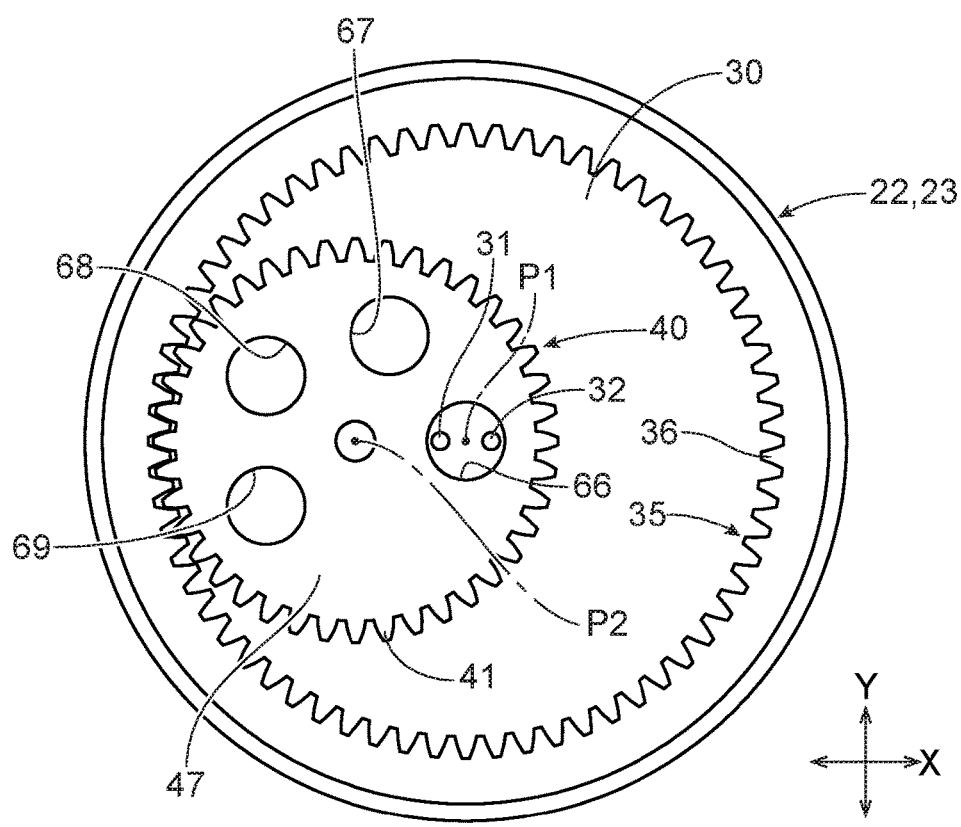
FIG. 15 shows another modified embodiment of the disc unit of the first embodiment.

In the modified embodiment shown in FIG. 15, light-transmission portions are formed by four round (circular) openings 66, 67, 68 and 69. Each of the four openings 66, 67, 68 and 69 has a diameter (inner diameter) that is greater than the distance between the first aperture 31 and the second aperture 32 in the aperture arrangement direction, and coincides with the first aperture 31 and the second aperture 32 at the above-described first through fourth angular positions. The openings 66, 67, 68 and 69, having the above-described shape, can have the same function as the above-described openings 43, 44, 45 and 46.

As can be understood from each modified embodiment, an opening(s) forming the light-transmission portion(s) in the shield control-plate 40 may be chosen from a variety of different shapes, providing that the opening(s) coincides with the first aperture 31 and the second aperture 32 and allows the first light bundle L1 and the second light bundle L2 to pass therethrough at a plurality of aperture arrangement directions.

Figure 16:
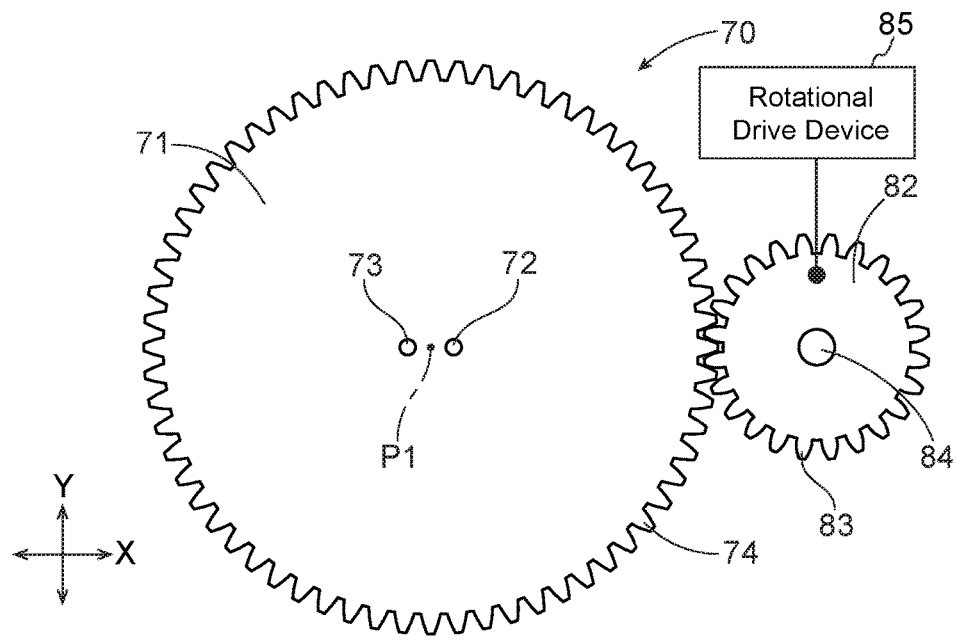
FIG. 16 is a front elevational view of a disc unit according to a second embodiment.
Figure 17:
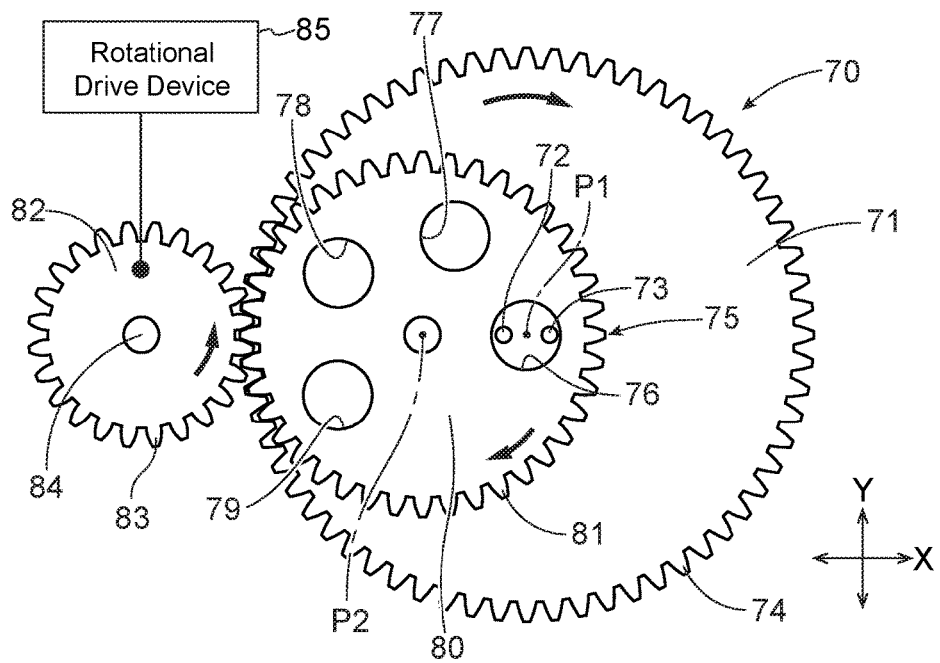
FIG. 17 is a rear elevational view of a disc unit according to a second embodiment.

FIG. 16 and FIG. 17 show a second embodiment of a disc unit 70 having a rotational-power transmission structure that differs from the first embodiment. Note that although FIG. 16 and FIG. 17 only show one disc unit 70, a disc unit 70 for the right eye and a disc unit 70 for the left eye are mounted onto a holder member 21 (refer to FIG. 5) in the same manner as the above-described disc units 22 and 23.

A measurement disc 71, constituting a rotational member, of the disc unit 70 corresponds to the measurement disc 10 in the refraction measuring apparatus shown in FIG. 1, and is rotatably supported about the first rotational center P1 relative to the annular rim 25 of the holder member 21. The measurement disc 71 is provided with a first aperture 72 and a second aperture 73 formed at symmetrical positions on either side of the first rotational center P1. The first aperture 72 and second aperture 73 each have the same configuration and function as the above-described first aperture 31 and second aperture 32. In other words, the arrangement direction of the first aperture 72 and the second aperture 73 is the aperture arrangement direction of the measurement disc 71.

A shield control-plate 75, constituting a second rotational member of the disc unit 70, is smaller in diameter than the measurement disc 71, and is rotatably supported, relative to the annular rim 25 of the holder member 21, about the second rotational center P2 that is positioned eccentrically from the first rotational center P1. In other words, the shield control-plate 75 is supported to only planetarily rotate about the second rotational center P2 independently from the measurement disc 71. Hence, the rotational support of the shield control-plate 75 differs from that of the above-described disc units 22 and 23 in that the shield control-plate 75 is rotatably supported on the holder member 21, which does not rotate, rather than the measurement disc 71, which is a rotational member.

In the shield control-plate 75, light-transmission portions are formed by four round (circular) openings 76, 77, 78 and 79. Each of the four openings 76, 77, 78 and 79 has a diameter (inner diameter) that is greater than the distance between the first aperture 72 and the second aperture 73 in the aperture arrangement direction. A region (section) of the shield control-plate 75 in the rotational direction between the opening 76 and the opening 79 defines a closed portion (light-shielding portion) 80, which does not allow light to pass therethrough.

The measurement disc 71 is an external gear member provided with outer teeth 74 on the outer periphery thereof. The shield control-plate 75 is an external gear member provided with outer teeth 81 on the outer periphery thereof. The outer teeth 74 have a larger number of teeth than the outer teeth 81, and the ratio thereof determined as 8:5 (e.g., the outer teeth 74 having sixty-four teeth and the outer teeth 81 having forty teeth).

The measurement disc 71 and the shield control-plate 75 are arranged in the forward/rearward direction, and the outer teeth 74 and the outer teeth 81 have a positional relationship so that they coincide at one position (the shield control-plate 75 is internally tangent to the measurement disc 71 in a front elevational view) in the rotational direction. Furthermore, a drive gear 82 is provided with outer teeth 83 which meshes with both the outer teeth 74 and the outer teeth 81 (at the above-mentioned "one position" at which these gears coincide). The drive gear 82 is rotatably supported about a shaft (axis) 84 that is parallel to the first rotational center P1 and the second rotational center P2. The shaft 84 is positioned on an extended straight line that connects the first rotational center P1 and the second rotational center P2, and the shaft 84 is positioned farther away from the first rotational center P1 than the second rotational center P2.

The outer teeth 74 of the measurement disc 71, the outer teeth 81 of the shield control-plate 75, and the drive gear 82 (outer teeth 83) form a gear mechanism so that the shield control-plate 75 rotates in association with the rotation of the measurement disc 71 via the drive gear 82; the gear mechanism rotates the shield control-plate 75 about the second rotational center P2 at a different rotational angle to the unit rotational-angle of the measurement disc 71 about the first rotational center P1.

The rotation of the drive gear 82 can be carried out via a manual operation by the examinee or the person conducting the examination. Alternatively, a rotational drive device 85, for use as a drive source such as a motor, etc., may be used to rotate the drive gear 82.

In the disc unit 70, conversely to the measurement disc 30 and the shield control-plate 40 of the disc unit 22 (23), the measurement disc 71 is provided on the front side (the side closer to the light-emission device 13) and the shield control-plate 75 is provided on the rear side (the side closer to the eye of the examinee). Therefore, the shield control-plate 75 controls how the first light bundle L1 and the second light bundle L2 proceed after passing through the first aperture 72 and the second aperture 73 of the measurement disc 71. In other words, the disc unit 22 (23) and the disc unit 70 differ with respect to which side of the measurement disc 30 and which side of the disc unit 70 the first and second light bundles L1 and L2 are shielded. Except for this difference, the disc unit 70 and the disc unit 22 (23) function in the same manner.

FIG. 16 and FIG. 17 show a state where the measurement disc 71 is at the first angular position, at which the aperture arrangement direction of the first aperture 72 and the second aperture 73 aligns with the X-direction (horizontal direction). In the shield control-plate 75, the opening 76 is at a position that coincides with the first aperture 72 and the second aperture 73. Accordingly, the first light bundle L1 and the second light bundle L2 that pass through the first aperture 72 and the second aperture 73 are able to proceed rearwardly through the opening 76, so that it is possible to measure the refractive properties of the eye at an orientation in the X-direction (horizontal direction).

Upon the drive gear 82 being rotatably driven from the first angular position, the measurement disc 71 and the shield control-plate 75 respectively rotate while changing the meshing position of the outer teeth 74 and 81 relative to the outer teeth 83. Specifically, the drive gear 82, the measurement disc 71 and the shield control-plate 75 respectively rotate in the directions indicated by the bold arrows in FIG. 17.

Upon the measurement disc 71 rotating from the first angular position by 45 degrees to arrive at the second angular position, the aperture arrangement direction of the first aperture 72 and the second aperture 73 is inclined by 45 degrees relative to the X-direction. Furthermore, due to the difference in the number of teeth between the outer teeth 74 and the outer teeth 81, the shield control-plate 75 rotates by a larger angle (72 degrees) than the measurement disc 71, so that the opening 77 coincides with the first aperture 72 and the second aperture 73. Accordingly, the first light bundle L1 and the second light bundle L2 that pass through the first aperture 72 and the second aperture 73 are able to proceed rearwardly through the opening 77, so that it is possible to measure the refractive properties of the eye at an intermediate orientation (45-degree direction) between the X-direction (horizontal direction) and the Y-direction (vertical direction).

Upon the measurement disc 71 rotating from the second angular position by 45 degrees to arrive at the third angular position, the aperture arrangement direction of the first aperture 72 and the second aperture 73 extends in the Y-direction. Furthermore, the shield control-plate 75 rotates by a larger angle (72 degrees) than the measurement disc 71, so that the opening 78 coincides with the first aperture 72 and the second aperture 73. Accordingly, the first light bundle L1 and the second light bundle L2 that pass through the first aperture 72 and the second aperture 73 are able to proceed rearwardly through the opening 78, so that it is possible to measure the refractive properties of the eye at an orientation in the Y-direction (vertical direction).

Upon the measurement disc 71 rotating from the third angular position by 45 degrees to arrive at the fourth angular position, the aperture arrangement direction of the first aperture 72 and the second aperture 73 inclines 45 degrees (i.e., 135 degrees) relative to the X-direction at a left-to-right inversed orientation to that of the above-mentioned second angular position. Furthermore, the shield control-plate 75 rotates by a larger angle (72 degrees) than the measurement disc 71, so that the opening 79 coincides with the first aperture 72 and the second aperture 73. Accordingly, the first light bundle L1 and the second light bundle L2 that pass through the first aperture 72 and the second aperture 73 are able to proceed rearwardly through the opening 79, so that it is possible to measure the refractive properties of the eye at an intermediate orientation (in a 135-degree direction) between the X-direction (horizontal direction) and the Y-direction (vertical direction).

Upon the measurement disc 71 rotating from the fourth angular position by 45 degrees to arrive at the fifth angular position, the aperture arrangement direction of the first aperture 72 and the second aperture 73 extends in the X-direction. More specifically, the positions of the first aperture 72 and the second aperture 73 are at the reverse left-to-right orientation relative to the first angular position shown in FIGS. 16 and 17. Furthermore, the shield control-plate 75 rotates by a larger angle (72 degrees) than the measurement disc 71, so that the closed portion 80 is positioned behind the first aperture 72 and the second aperture 73. Accordingly, the first light bundle L1 and the second light bundle L2 that pass through the first aperture 72 and the second aperture 73 are shielded (blocked) by the closed portion 80.

Accordingly, by setting the measurement disc 71 to the fifth angular position in one of the right-eye disc unit 70 and the left-eye disc unit 70, and successively rotating the measurement disc 71 in the other of the right-eye disc unit 70 and the left-eye disc unit 70 from the first through fourth angular positions, the refractive properties of each eye can be measured at each orientation.

The disc unit 70 for the right eye and the disc unit 70 for the left eye are separately provided for use, and since there is no replacing or exchanging of components when changing to one eye to the other for testing, there is no need to perform an operation in which components are removed and attached (replaced/exchanged). Furthermore, in each of the disc unit 70, since the all of the operations of selecting the orientations for measuring the refractive properties, and setting a shielded state, are performed only by the rotation of the drive gear 82, the measurement jig 20 exhibits superior workability.

Furthermore, by using the disc units 70 having the same structure for the right eye and for the left eye, respectively, the number of components can be reduced, thereby reducing manufacturing costs.

Although the openings 76, 77, 78 and 79 shown in FIGS. 16 and 17 each are round (circular) in shape, openings having a shape other than a round shape may be used as a light-transmission portion, as in the first embodiment of the disc unit 22 (23).

The above-described disc units 22 and 23 of the first embodiment and the above-described disc units 70 of the second embodiment are fitted onto (worn by) the examinee so that each first rotational center P1, which is the rotational center of the measurement disc 30 (71), and the associated axis of vision Q (FIG. 1) of the examinee's eye align, and a set of one first aperture 31 (72) and one second aperture 32 (73) is provided on the measurement disc 30 (71). Furthermore, the transmission of the first light bundle L1 and the second light bundle L2 through the first aperture 72 and the second aperture 73 is controlled by using the light-transmission portions (the plurality of openings or a single continuous opening) and a light-shielding portion (closed portion) that are provided on the shield control-plate 40 (75) which is overlapped with the measurement disc 30 (71).

A measurement disc 100 according to a third embodiment, which differs from the above-described first and second embodiments, is shown in FIGS. 18 through 22. Note that although FIGS. 18 through 22 only show one measurement disc 100, a measurement disc 100 for the right eye and a measurement disc 100 for the left eye are mounted onto the holder member 21 (refer to FIG. 5) in the same manner as the above-described disc unit 22 and disc unit 23.

The measurement disc 100 is rotatably supported, relative to the annular rim 25 of the holder member 21, about a third rotational center P3 that is positioned eccentrically from the axis of vision Q. The measurement disc 100 is provided, at different positions in the rotational direction about the third rotational center P3 and at radial directions from the third rotational center P3, with first and second apertures 101A and 102A, first and second apertures 101B and 102B, first and second apertures 101C and 102C, and first and second apertures 101D and 102D. In other words, the measurement disc 100 is provided with four groups of first apertures (101A through 101D) and second apertures (102A through 102D). Furthermore, the measurement disc 100 is provided with a closed portion (light-shielding portion) 103, which does not allow light to pass therethrough, at an area (section) in the rotational direction other than that of the four groups of the first and second apertures (101A through 101D and 102A through 102D).

The aperture arrangement directions of each of the four groups of the first and second apertures (101A through 101D and 102A through 102D) are mutually parallel to each other. Furthermore, the mutual distances between the centers of the respective four groups of the first and second apertures (101A through 101D and 102A through 102D) are mutually the same, and each distance thereof is determined in order for the Scheiner principle to manifest.

The rotation of the measurement disc 100 can be carried out via a manual operation by the examinee or the person conducting the examination. Alternatively, a rotational drive device 104 (only shown in FIG. 18), for use as a drive source such as a motor, etc., may be used to rotate the measurement disc 100.

Figure 18:
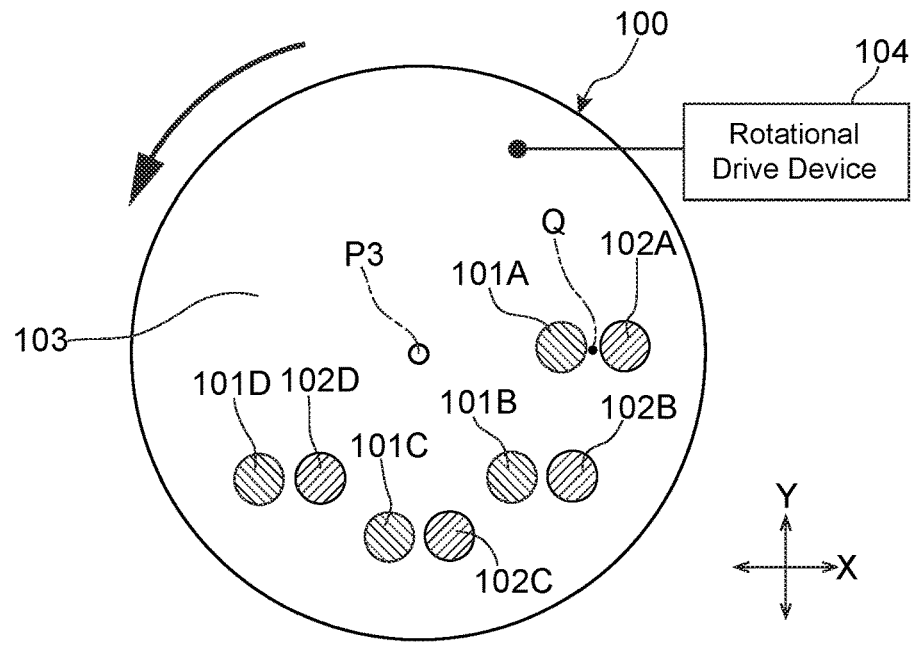
FIG. 18 shows a state at which a measuring disc, of a third embodiment, is at a first angular position.

FIG. 18 shows a state in which the measurement disc 100 is positioned at the first angular position. At this position, the first and second apertures 101A and 102A are arranged in a symmetrical positional relationship on either side of the axis of vision Q in the X-direction. In other words, the aperture arrangement direction of the first and second apertures 101A and 102A aligns with the X-direction. Accordingly, based on the image (the visual marker images 14M and 15M) formed on the retina by the first light bundle L1 and the second light bundle L2 (refer to FIG. 1) passing through the first and second apertures 101A and 102A, respectively, the refractive properties of the eye can be measured at an orientation in the X-direction (horizontal direction), which corresponds to the aperture arrangement direction of the first and second apertures 101A and 102A.

In the state shown in FIG. 18, the aperture arrangement directions of the respective apertures of the other three groups (the first and second apertures 101B and 102B, the first and second apertures 101C and 102C, and the first and second apertures 101D and 102D) extend in the X-direction in the same manner as the first and second apertures 101A and 102A. Furthermore, the distance in the X-direction between the centers of the first and second apertures 101B and 102B, the distance in the X-direction between the centers of the first and second apertures 101C and 102C, and the distance in the X-direction between the centers of the first and second apertures 101D and 102D are the same as the distance in the X-direction between the centers of the first and second apertures 101A and 102A.

Figure 19:
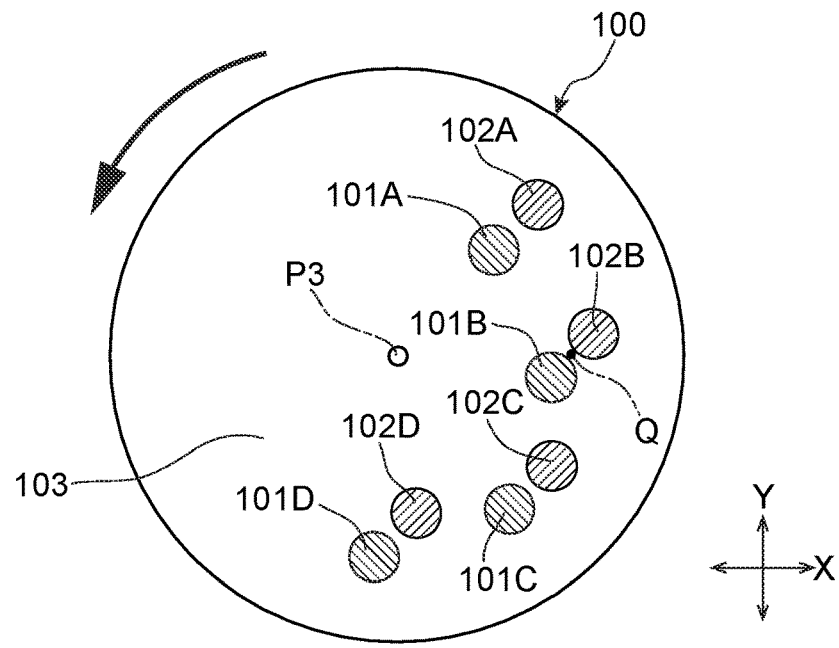
FIG. 19 shows a state at which the measuring disc, of the third embodiment, is at a second angular position.

FIG. 19 shows a state where the measurement disc 100 has been rotated, by 45 degrees from the first angular position shown in FIG. 18, in the anti-clockwise direction about the third rotational center P3 in a front elevational view, to the second angular position. In this state, the apertures that are positioned on either side of the axis of vision Q are changed (switched) to the first and second apertures 101B and 102B, so that the aperture arrangement direction of the first and second apertures 101B and 102B is inclined at 45 degrees upward, toward the right side, relative to the X-direction.

Accordingly, by setting the measurement disc 100 to the position (the second angular position) shown in FIG. 19, based on the image (the visual marker images 14M and 15M) formed on the retina by the first light bundle L1 and the second light bundle L2 (refer to FIG. 1) passing through the first and second apertures 101B and 102B, respectively, the refractive properties of the eye can be measured at a first intermediate orientation (a 45-degree direction), which corresponds to the aperture arrangement direction of the first and second apertures 101B and 102B, between the X-direction (horizontal direction) and the Y-direction (vertical direction).

Figure 20:
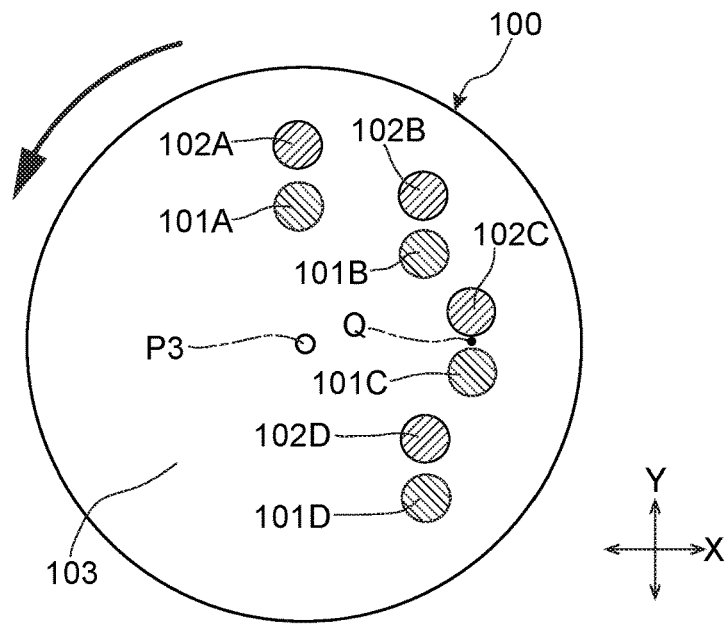
FIG. 20 shows a state at which the measuring disc, of the third embodiment, is at a third angular position.

FIG. 20 shows a state where the measurement disc 100 has been rotated, by 45 degrees from the second angular position shown in FIG. 19, in the anti-clockwise direction about the third rotational center P3 in a front elevational view, to the third angular position. In this state, the apertures that are positioned on either side of the axis of vision Q are changed (switched) to the first and second apertures 101C and 102C, so that the aperture arrangement direction of the first and second apertures 101C and 102C extends in the Y-direction.

Accordingly, by setting the measurement disc 100 to the position (the third angular position) shown in FIG. 20, based on the image (the visual marker images 14M and 15M) formed on the retina by the first light bundle L1 and the second light bundle L2 (refer to FIG. 1) passing through the first and second apertures 101C and 102C, respectively, the refractive properties of the eye can be measured in the Y-direction (vertical direction), which corresponds to the aperture arrangement direction of the first and second apertures 101C and 102C.

Figure 21:
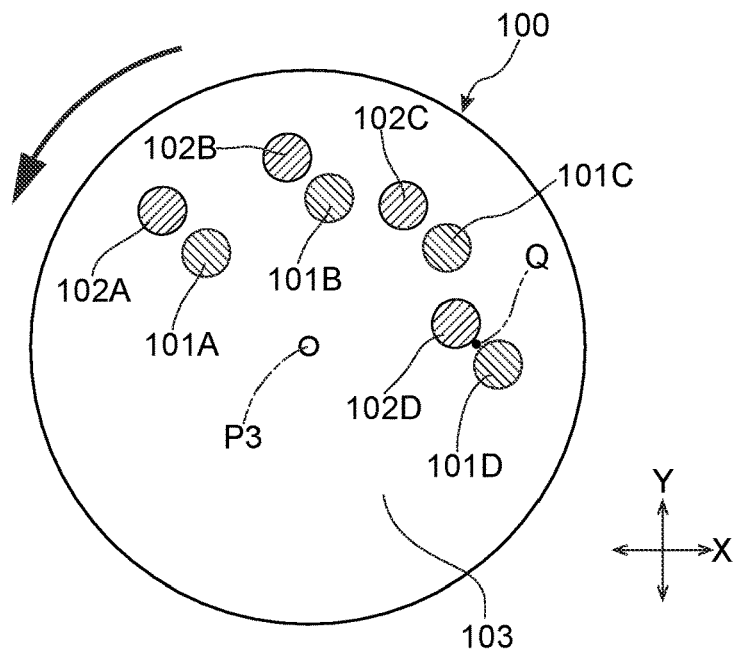
FIG. 21 shows a state at which the measuring disc, of the third embodiment, is at a fourth angular position.

FIG. 21 shows a state where the measurement disc 100 has been rotated, by 45 degrees from the third angular position shown in FIG. 20, in the anti-clockwise direction about the third rotational center P3 in a front elevational view, to the fourth angular position. In this state, the apertures that are positioned on either side of the axis of vision Q are changed (switched) to the first and second apertures 101D and 102D, so that the aperture arrangement direction of the first and second apertures 101D and 102D is inclined at 45 degrees downward, toward the right side, relative to the X-direction. Since this aperture arrangement direction has a left-to-right inversed orientation relative to the aperture arrangement direction of the second angular position (FIG. 19), the aperture arrangement direction has changed by 135 degrees relative to the aperture arrangement direction, set to 0 degrees, of the first angular position (FIG. 18).

Accordingly, by setting the measurement disc 100 to the position (the fourth angular position) shown in FIG. 21, based on the image (the visual marker images 14M and 15M) formed on the retina by the first light bundle L1 and the second light bundle L2 (refer to FIG. 1) passing through the first and second apertures 101D and 102D, respectively, the refractive properties of the eye can be measured at a second intermediate orientation (a 135-degree direction), which corresponds to the aperture arrangement direction of the first and second apertures 101D and 102D, between the X-direction (horizontal direction) and the Y-direction (vertical direction).

Figure 22:
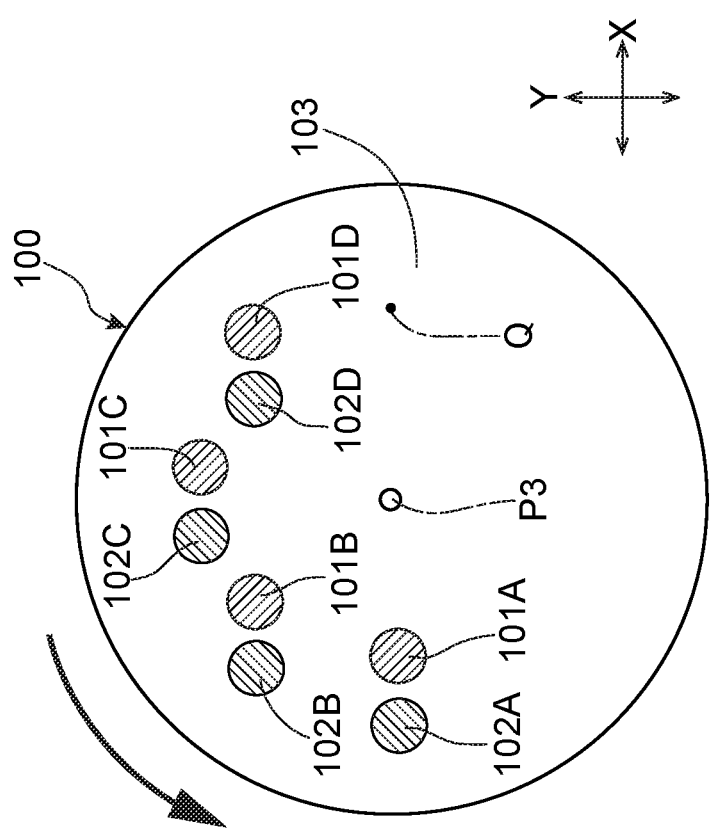
FIG. 22 shows a state at which the measuring disc, of the third embodiment, is at a fifth angular position.

FIG. 22 shows a state where the measurement disc 100 has been rotated, by 45 degrees from the fourth angular position shown in FIG. 21, in the anti-clockwise direction about the third rotational center P3 in a front elevational view, to the fifth angular position. In this state, the closed portion 103 is positioned on the axis of vision Q, and the surrounding area thereof, so that the transmission of first light bundle L1 and the second light bundle L2 (FIG. 1) is shielded (blocked) by the closed portion 103 in the field-of-view area of the examinee.

Accordingly, by setting the measurement disc 100 to the position (the fifth angular position) shown in FIG. 22, each of the four groups of the first and second apertures (101A through 101D and 102A through 102D) are in a light-shielded state in which the first light bundle L1 and the second light bundle L2 cannot be transmitted to the retina.

As described above, measurement of the refractive properties of the eye can be measured at a plurality of directions (FIGS. 18 through 21) and the first light bundle L1 and the second light bundle L2 can be shielded (FIG. 22) by rotating the measurement disc 100 about the third rotational center P3. Since the measurement disc 100 for the right eye and the measurement disc 100 for the left eye are separately provided for use, and since there is no replacing or exchanging of components when changing to one eye to the other for testing, there is no need to perform an operation in which components are removed and attached (replaced/exchanged). Furthermore, in each of the measurement disc 100, since the all of the operations of selecting the orientations for measuring the refractive properties, and setting a shielded state, are performed only by the rotation of the measurement disc 100 itself; the measurement disc 100 exhibits superior workability. Furthermore, by using the measurement disc 100, which has the same structure, for the right eye and for the left eye, respectively, the number of components can be reduced, thereby reducing manufacturing costs.

Furthermore, by appropriately arranging a plurality of groups of first apertures (101A through 101D) and second apertures (102A through 102D), all functions related to the transmission and shielding of the first light bundle L1 and the second light bundle L2 can be consolidated onto a single measurement disc 100. Accordingly, the number of components for constructing the refraction measurement apparatus can be reduced, thereby simplifying the structure and reducing costs.

As described above, the refraction measurement apparatus of each disclosed embodiment (modified embodiments included) of the present disclosure can reduce time and effort required in measuring the refractive properties of both eyes of the examinee. In particular, since the change in measurement orientation and the switching to a light-shielded state can be carried out simply by a series of rotational operations, a superior workability is exhibited in the case where a manual operation is performed. Furthermore, also in the case where the rotational members are rotatably driven by a rotational drive device (27, 85 and 104), a rotational drive device having a miniaturized, light-weight and low-cost construction can be employed.

Furthermore, since the measurement jig (20) worn by the examinee can be miniaturized, light-weight, and constructed from a small number of components, a large installment space or a high-cost installation is unnecessary; moreover, there is the advantage of the physical burden on the examinee being able to be reduced.

Although the above descriptions are based on specific embodiments shown in the drawings, the present invention is not limited thereto; various modifications and changes are permissible, being within the spirit and scope of the invention claimed.

For example, the number of orientations for measuring the refractive properties of the eye may be a number other than the four orientations disclosed in the above embodiments. As an example, in addition to the horizontal direction (X-direction) and the vertical direction (Y-direction), it is possible for only one intermediate orientation to be set between the horizontal direction and the vertical direction to perform measurements at three different orientations. Alternatively, it is possible to increase the number of intermediate orientations to perform measurements at five or more orientations. The arrangement of the first and second apertures in the measurement disc, the configuration of the light-transmission portion(s) and the light-shielding portion in the shield control-plate, and the relative angular settings (the number of teeth in the case where a gear mechanism is employed) for when the measurement disc and the shield control-plate are respectively rotated, can be modified in accordance with the number of measurement orientations.

What is claimed is:

1. A refraction measuring apparatus that measures refractive properties of an eye based on respective images formed by first and second light bundles, emanating from a light emitter, the first and second light bundles respectively passing through first and second apertures, provided at a same distance away from the light emitter, and concurrently incident on the eye, the refraction measuring apparatus comprising, at respective positions corresponding to a pair of the eyes:
a first rotational member, rotatably supported on a support member about a first rotational center, provided with the first aperture and the second aperture on either side of the first rotational center;
a second rotational member, rotatably supported about a second rotational center, at a different position from the first rotational center, the second rotational member provided with at least one light-transmission portion and a light-shielding portion at different positions in a rotational direction about the second rotational center,
wherein when the first rotational member is rotated relative to the support member, the second rotational member rotates in association with the rotation of the first rotational member, and
wherein, while an aperture arrangement direction of the first and second apertures changes in accordance with the rotation of the second rotational member, the refraction measuring apparatus enters one of:
a light-transmission state in which the light-transmission portion coincides with the first and second apertures to allow the first and second light bundles to pass through the first and second apertures; and
a light-shielding state in which the light-shielding portion coincides with the first and second apertures to shield the first and second light bundles.

2. The refraction measuring apparatus according to claim 1, further provided with a gear mechanism for rotating the second rotational member about the second rotational center at a different angle of rotation to a unit angle-of-rotation of the first rotational member about the first rotational center.

3. The refraction measuring apparatus according to claim 2, wherein annular internal teeth, centered about the first rotational center, are fixedly provided on the support member,
wherein the second rotational member is rotatably supported on the first rotational member about the second rotational center,
wherein the second rotational member is provided with outer teeth which mesh with the internal teeth, and
wherein when the first rotational member rotates, the second rotational member rotates while changing a meshing position between the internal teeth and the outer teeth.

4. The refraction measuring apparatus according to claim 2, wherein the second rotational member is rotatably supported on the support member about the second rotational center,
wherein the first rotational member and the second rotational member are respectively provided with outer teeth, each having a mutually different number of teeth,
wherein a drive gear is further provided which meshes with the outer teeth of the first rotational member and the outer teeth of the second rotational member, and
wherein when the drive gear rotates, the first rotational member and the second rotational member rotate while changing a meshing position between the drive gear and the respective outer teeth of the first rotational member and the second rotational member.

5. The refraction measuring apparatus according to claim 1, wherein the light-transmission portion comprises a plurality of openings formed through the second rotational member at different positions in a rotational direction about the second rotational center, and
wherein, in the light-transmission state, the first and second apertures coincide with each respective opening of the plurality of openings, oriented in a plurality of aperture arrangement directions about the first rotational center, to thereby allow the first and second light bundles to pass through the first and second apertures.

6. The refraction measuring apparatus according to claim 5, wherein four of the openings are provided in the second rotational member, wherein the first and second apertures coincide with each respective opening of the four openings per a 45-degree rotation of the first rotational member.

7. The refraction measuring apparatus according to claim 1, wherein the light-transmission portion comprises a continuous opening formed continuously in a rotational direction about the second rotational center, and
wherein, in the light-transmission state, the first and second apertures allow the first and second light bundles to pass therethrough while continuously changing the aperture arrangement direction within a range defined by the continuous opening.

8. A refraction measuring apparatus that measures refractive properties of an eye based on respective images formed by first and second light bundles, emanating from a light emitter, the first and second light bundles respectively passing through first and second apertures, provided at a same distance away from the light emitter, and concurrently incident on the eye, the refraction measuring apparatus comprising:

rotational members, rotatably supported at positions that correspond to a pair of the eyes, respectively, the rotational members including:
- a first rotational member, rotatably supported on a support member about a first rotational center, provided with the first aperture and the second aperture on either side of the first rotational center;
- a second rotational member, rotatably supported about a second rotational center, at a different position from the first rotational center, the second rotational member provided with at least one light-transmission portion and a light-shielding portion at different positions in a rotational direction about the second rotational center, wherein when the first rotational member is rotated relative to the support member, the second rotational member rotates in association with the rotation of the first rotational member, wherein each rotational member is provided with a plurality of groups of the first and second apertures, and a light-shielding portion, at respective positions that are positioned eccentrically from the rotational center of an associated rotational member, and wherein, while respective aperture arrangement directions of the plurality of groups of the first and second apertures change in accordance with a change in an angular position of the associated rotational member in the rotational direction, the refraction measuring apparatus enters one of:
- a light-transmission state in which the first and second light bundles pass through, at either side of an axis of vision, one group of the first and second apertures at a time; and
- a light-shielding state in which the light-shielding portion shields the first and second light bundles from a field-of-view area.

9. The refraction measuring apparatus according to claim 8, wherein each rotational member is provided with four groups of the first and second apertures.

10. The refraction measuring apparatus according to claim 8, wherein the aperture arrangement directions of each of the groups of the first and second apertures, of each rotational member, are mutually parallel to each other.

11. The refraction measuring apparatus according to claim 8, the mutual distances between the centers of the respective groups of the first and second apertures are mutually the same.

* * * * *